(12) United States Patent
Famodu et al.

(10) Patent No.: US 6,436,657 B1
(45) Date of Patent: Aug. 20, 2002

(54) POLYNUCLEOTIDES ENCODING AMINOMETHYLTRANSFERASES

(75) Inventors: Omolayo O. Famodu, Newark, DE (US); Emil M. Orozco, Jr., West Grove, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/465,558

(22) Filed: Dec. 17, 1999

Related U.S. Application Data

(60) Provisional application No. 60/112,734, filed on Dec. 18, 1998.

(51) Int. Cl.[7] ............... C07H 21/04; C12N 9/10; C12N 15/00; C12N 5/10; C12N 7/00; C12N 15/82; C12Q 1/48; C12P 19/34

(52) U.S. Cl. ............... 435/15; 435/193; 435/320.1; 435/419; 435/235.1; 435/468; 435/91.2; 435/252.3; 435/325; 435/254.11; 435/440; 536/23.2; 800/295; 800/288

(58) Field of Search ............... 536/23.2; 435/193.15, 435/320.1, 419, 235.1, 468, 91.2, 252.3, 325, 254.11, 440; 800/295, 288

(56) References Cited

PUBLICATIONS

Turner et al., (1992) J. Biol. Chem., 267:13528–13534.
Schnorr et al., (1994) Plant J. 6:113–121.
Tibbetts and Appling (1997) Arch. Biochem. Biophys. 340:195–200.
Nour and Rabinowitz (1991) J. Boiol. Chem. 266:18363–18369.
Bourguignon et al., (1993) Eur. J. Biochem. 217:377–386.
NCBI General Identifier No. 1707998 Oct., 1998.
Plant Phys. 107(1):271–272 (1995).
NCBI General Identifier N. 462187 Feb. 1994.
NCBI General Identifier No. 1346155 Feb. 1996.
NCBI General Identifier No. 1709923 Oct. 1996.
NCBI General Identifier No. 1709922 Oct. 1996.
NCBI General Identifier No. 2245095 Aug. 1999.
NCBI General Identifier No. 2072373 Jul. 1999.
Microbiology 145(P. 3):621–631 (1999).
NCBI General Identifier No. 1172763 Nov. 1995.
Science 269(5223):496–512 (1995).
NCBI General Identifier No. 3033398 Apr. 2000.
Nature 402 (6763): 761–768 (1999).
NCBI General Identifier No. 131638 Jul. 1999.
J. Biol. Chem. 262(17):8274–8287 (1987).
Microbiology 142(Pt 11):3027–3031 (1996).
NCBI General Identifier No. 2507455 Dec. 1992.
J. Biol. Chem. 267(23):16292–16296 (1992).
NCBI General Identifier No. 5921663 Sep., 1999.
Plant Phys. 121(1):312 (1999).
NCBI General Identifier No. 3334197 Jul. 1998.
NCBI General Identifier No. 1346123 Feb. 1996.
Plant Mol. Biol. 27(6):1215–1220 (1995).
NCBI General Identifier No. 1707878 Oct. 1996.
Plant Phys. 104(3):1079–1080 (1994).
NCBI General Identifier No. 1346121 Feb. 1996.
NCBI General Identifier No. 3915699 Feb. 1996.
Plant Mol. Biol. 37(2):309–318 (1998).
NCBI General Identifier No. 3334202 Jul. 1998.
NCBI General Identifier No. 3157944 May 1998.
Bourguignon et al., (1988) Biochem. J. 255:169–178.
Boger et al., (1997) Bioorg. Med. Chem. 5:1839–1846.
Freudenberg and Andreesen (1989) J. Bacteriol. 171:2209–2215.

*Primary Examiner*—Rebecca E. Prouty
*Assistant Examiner*—David Steadman

(57) ABSTRACT

This invention relates to an isolated nucleic acid fragment encoding a tetrahydrofolate metabolic enzyme. The invention also relates to the construction of a chimeric gene encoding all or a portion of the tetrahydrofolate metabolic enzyme, in sense or antisense orientation, wherein expression of the chimeric gene results in production of altered levels of the tetrahydrofolate metabolic enzyme in a transformed host cell.

14 Claims, No Drawings

POLYNUCLEOTIDES ENCODING AMINOMETHYLTRANSFERASES

This application claims the benefit of U.S. Provisional Application No. 60/112,734, filed Dec. 18, 1998.

FIELD OF THE INVENTION

This invention is in the field of plant molecular biology. More specifically, this invention pertains to nucleic acid fragments encoding tetrahydrofolate metabolic enzymes in plants and seeds.

BACKGROUND OF THE INVENTION

Tetrahydrofolic acid and its derivatives $N^5,N^{10}$-methylenetetrahydrofolate, $N^5,N^{10}$-methenyltetrahydrofolate, $N^{10}$-formyltetrahydrofolate, and $N^5$-methyltetrahydrofolate are the biologically-active forms of folic acid, a four-electron-oxidized form of tetrahydrofolate (THF). The tetrahydrofolates are coenzymes which are not enzyme-bound and are specialized cosubstrates for a variety of enzymes involved in one-carbon metabolism. THF is a 6-methylpterin derivative linked to p-aminobenzoic acid and glutamic acid residues. Its function is to transfer C1 units in several oxidation states. The C1 units are covalently attached to THF at its N5 and/or N10 positions and enter into the THF pool through the conversion of serine to glycine by serine hydroxymethyl transferase and the cleavage of glycine by glycine synthase. A C1 unit in the THF pool can have several outcomes: it may be used in the conversion of the deoxynucleotide dUMP to dTMP by thymidylate synthase, it may be reduced for the synthesis of methionine, or it may oxidized for the use in the synthesis of purines, since the purine ring from ATP is involved in histidine biosynthesis.

Serine hydroxymethylase, phosphoribosylglycinamide formyltransferase, phosphoribosylaminoimidazolecarboxamide formyltransferase, formate-tetrahydrofolate ligase and aminomethyltransferase are five enzymes involved in tetrahydrofolate metabolism. Serine hydroxymethylase (EC 2.1.2.1) is also called serine aldolase, glycine hydroxymethyltransferase or threonine aldolase. This enzyme catalyzes the conversion of 5,10-methylenetetrahydrofolate and glycine to tetrahydrofolate and L-serine. This enzyme is involved in multiple pathways such as glycine, serine and threonine metabolism, lysine degradation, cyano-amino acid metabolism and one carbon pool by folate and methane metabolism. In pea, two mitochondrial forms and a non-mitochondrial form of the enzyme are found. The mRNA appears to be expressed predominantly in leaves (Turner et al. (1992) *J. Biol. Chem.* 267:13528–13534).

Phosphoribosylglycinamide formyltransferase (EC 2.1.2.2), also called GAR transformylase or 5'-phosphoribosylglycinamide transformylase is involved in the purine metabolism pathway and the one carbon pool folate. It is located in the chloroplast and catalyzes the conversion of 10-formyltetrahydrofolate and 5'-phosphoribosylglycinamide into tetrahydrofolate and 5'-phosphoribosyl-N-formylglycinamide. It is the third enzyme in the 10-step de novo purine biosynthetic pathway and its cDNA has been identified in *Arabidopsis thaliana* where it was shown to encode a single monofunctional enzyme (Schnorr et al. (1994) *Plant J.* 6:113–121).

Phosphoribosylaminoimidazolecarboxamide formyltransferase (EC 2.1.2.3), also called 5-aminoimidazole-4-carboxamide ribonucleotide (AICAR) transformylase, catalyzes the ninth step of the de novo purine biosynthesis pathway converting 10-formyltetrahydrofolate and 1-(5'-phosphoribosyl)-5-amino-4-imidazolecarboxamide to tetrahydrofolate and 1-(5'-phosphoribosyl)-5-formamido-4-inidazolecarboxamide. Two *Saccharomyces cerevisiae* genes encoding isozymes of AICAR transformylase have been described. Yeast is the only organism where two different isozymes have been identified (Tibbetts and Appling (1997) *Arch. Biochem. Biophys.* 340:195–200).

Formate—tetrahydrofolate ligase (EC 6.3.4.3) is also called formyltetrahydrofolate synthetase or 10-formyltetrahydrofolate synthetase. In eukaryotes it occurs as a trifunctional enzyme also having methylenetetrahydrofolate dehydrogenase (EC 1.5.1.5) and methenyltetrahydrofolate cyclohydrolase (EC 3.5.4.9) activities. It is involved in the glyoxylate and dicarboxylate metabolism pathways and one carbon pool by folate and folate biosynthesis. The first plant formate-tetrahydrofolate ligase has been purified from spinach leaves where it appears to be monofunctional and where it was found to be a dimer with a subunit molecular weight of 67,000 (Nour and Rabinowitz (1991) *J. Biol. Chem.* 266:18363–18369).

Aminomethyltransferase (EC 2.1.2.10), is also called T-Protein of the glycine cleavage system, tetrahydrofolate aminomethyltransferase or S-aminomethyldihydrolipoylprotein (6S)-tetrahydrofolate aminomethyltransferase (ammonia-forming). It catalyzes the conversion of (6S)-tetrahydrofolate and S-aminomethyldihydrolipoylprotein to (6R)-5,10-methylenetetrahydrofolate, ammonia and Dihydrolipoylprotein. Aminomethyltransferase from pea has been purified to homogeneity and its cDNA identified. Using Northern blot analysis, a high steady state level of mRNA was found to accumulate in green leaves compared to etiolated leaves. The mRNA was also found in roots where the protein is detectable by Western blot analysis (Bourguignon et al. (1993) *Eur. J. Biochem.* 217:377–386).

Because these enzymes are involved in tetrahydrofolate metabolism, amino acid synthesis, fatty acid biosynthesis and de novo synthesis of purines, inhibition of their activity may be lethal, thus suggesting that they would be attractive herbicide targets. Production of these plant enzymes in bacteria for use in a high throughput screen for chemical inhibitors would be desirable. Alternatively, overproduction of these enzymes in transgenic plants could be used to enhance the production of many secondary metabolites, amino acids, purine nucleic acids and vitamins. Accordingly, the availability of nucleic acid sequences encoding all or a portion of an enzyme involved in tetrahydrofolate metabolism would facilitate studies to better understand tetrahydrofolate metabolism in plants and provide genetic tools to enhance the production of secondary metabolites, amino acids and vitamins. These enzymes may also provide targets to facilitate design and/or identification of inhibitors of tetrahydrofolate metabolism that may be useful as herbicides.

SUMMARY OF THE INVENTION

The present invention relates to isolated polynucleotides comprising a nucleotide sequence encoding a polypeptide of at least 100 amino acids that has at least 90% identity based on the Clustal method of alignment when compared to a serine hydroxymethylase polypeptide selected from the group consisting of SEQ ID NOs:2, 4, 6, 8, 34, 36, 38, and 40. The present invention also relates to an isolated polynucleotide comprising the complement of the nucleotide sequences described above.

The present invention relates to isolated polynucleotides comprising a nucleotide sequence encoding a polypeptide of at least 70 amino acids that has at least 80% identity based on the Clustal method of alignment when compared to a phosphoribosylglycinamide formyltransferase polypeptide selected from the group consisting of SEQ ID NOs:10, 12, 42, 44, and 46. The present invention also relates to an isolated polynucleotide comprising the complement of the nucleotide sequences described above.

The present invention relates to isolated polynucleotides comprising a nucleotide sequence encoding a polypeptide of at least 70 amino acids that has at least 90% identity based on the Clustal method of alignment when compared to a phosphoribosylamino-imidazolecarboxamide formyltransferase polypeptide selected from the group consisting of SEQ ID NOs:14, 16, 48, 50, 52, and 54. The present invention also relates to an isolated polynucleotide comprising the complement of the nucleotide sequences described above.

The present invention relates to isolated polynucleotides comprising a nucleotide sequence encoding a polypeptide of at least 70 amino acids that has at least 90% identity based on the Clustal method of alignment when compared to a formate—tetrahydrofolate ligase polypeptide selected from the group consisting of SEQ ID NOs:18, 20, 22, 24, 56, 58, 60, and 62. The present invention also relates to an isolated polynucleotide comprising the complement of the nucleotide sequences described above.

The present invention relates to isolated polynucleotides comprising a nucleotide sequence encoding a polypeptide of at least 60 amino acids that has at least 90% identity based on the Clustal method of alignment when compared to an aminomethyltransferase polypeptide selected from the group consisting of SEQ ID NOs:26, 28, 30, 32, 64, 66, 68, and 70. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, and 69 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, and 70. The present invention also relates to an isolated polynucleotide comprising a nucleotide sequences of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a serine hydroxymethylase polypeptide of at least 100 amino acids comprising at least 90% homology based on the Clustal method of alignment compared to a polypeptide selected from the group consisting of SEQ ID NOs:2, 4, 6, 8, 34, 36, 38, and 40.

The present invention relates to a phosphoribosylglycinamide formyltransferase polypeptide of at least 70 amino acids comprising at least 80% homology based on the Clustal method of alignment compared to a polypeptide selected from the group consisting of SEQ ID NOs:10, 12, 42, 44, and 46.

The present invention relates to a phosphoribosylaminoimidazolecarboxamide formyltransferase polypeptide of at least 70 amino acids comprising at least 90% homology based on the Clustal method of alignment compared to a polypeptide selected from the group consisting of SEQ ID NOs:14, 16, 48, 50, 52, and 54.

The present invention relates to a formate—tetrahydrofolate ligase polypeptide of at least 70 amino acids comprising at least 90% homology based on the Clustal method of alignment compared to a polypeptide selected from the group consisting of SEQ ID NOs:18, 20, 22, 24, 56, 58, 60, and 62.

The present invention relates to an aminomethyltransferase polypeptide of at least 60 amino acids comprising at least 90% homology based on the Clustal method of alignment compared to a polypeptide selected from the group consisting of SEQ ID NOs:26, 28, 30, 32, 64, 66, 68, and 70.

The present invention relates to a method of selecting an isolated polynucleotide that affects the level of expression of a tetrahydrofolate metabolic enzyme polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a serine hydroxymethylase, a phosphoribosylglycinamide formyltransferase, a phosphoribosylaminoimidazolecarboxamide formyltransferase, a formate—tetrahydrofolate ligase or an aminomethyltransferase polypeptide in the host cell containing the isolated polynucleotide; and (d) comparing the level of the tetrahydrofolate metabolic enzyme polypeptide in the host cell containing the isolated polynucleotide with the level of the serine hydroxymethylase, the phosphoribosylglycinamide formyltransferase, the phosphoribosylaminoimidazolecarboxamide formyltransferase, the formate—tetrahydrofolate ligase or the aminomethyltransferase polypeptide in the host cell that does not contain the isolated polynucleotide.

The present invention relates to a method of obtaining a nucleic acid fragment encoding a substantial portion of a serine hydroxymethylase, a phosphoribosylglycinamide formyltransferase, a phosphoribosylaminoimidazolecarboxamide formyltransferase, a formate—tetrahydrofolate ligase or an aminomethyltransferase polypeptide gene, preferably a plant serine hydroxymethylase, phosphoribosylglycinamide formyltransferase, phosphoribosylaminoimidazolecarboxamide formyltransferase, formate—tetrahydrofolate ligase or aminomethyltransferase polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27,29, 31, 33, 35, 37, 39,41,43,45,47,49, 51, 53, 55, 57, 59, 61, 63, 65, 67, 69 and the complement of such nucleotide sequences; and amplifying a nucleic acid fragment (preferably a cDNA inserted in a cloning vector) using the oligonucleotide primer. The amplified nucleic acid fragment preferably will encode a portion of a serine hydroxymethylase, a phosphoribosylglycinamide formyltransferase, a phosphoribosylaminoimidazolecarboxamide formyltransferase, a formate—tetrahydrofolate ligase or an aminomethyltransferase amino acid sequence.

The present invention also relates to a method of obtaining a nucleic acid fragment encoding all or a substantial portion of the amino acid sequence encoding a serine hydroxymethylase, a phosphoribosylglycinamide formyltransferase, a phosphoribosylaminoimidazolecarboxamide formyltransferase, a formate—tetrahydrofolate ligase or an aminomethyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a serine hydroxymethylase, a phosphoribosylglycinamide formyltransferase, a phosphoribosylaminoimidazolecarboxamide formyltransferase, a formate—tetrahydrofolate ligase or an aminomethyltransferase, the method comprising the steps of: (a) transforming a host cell with a chimeric gene comprising a nucleic acid fragment encoding a serine hydroxymethylase, a phosphoribosylglycinamide formyltransferase, a phosphoribosylaminoimidazolecarboxamide formyltransferase, a formate—tetrahydrofolate ligase or an aminomethyltransferase, operably linked to suitable regulatory sequences; (b) growing the transformed host cell under conditions that are suitable for expression of the chimeric gene wherein expression of the chimeric gene results in production of serine hydroxymethylase, phosphoribosylglycinamide formyltransferase, phosphoribosylaminoimidazolecarboxamide formyltransferase, formate—tetrahydrofolate ligase or aminomethyltransferase in the transformed host cell; (c) optionally purifying the serine hydroxymethylase, the phosphoribosylglycinamide formyltransferase, the phosphoribosylaminoimidazolecarboxamide formyltransferase, the formate—tetrahydrofolate ligase or the aminomethyltransferase expressed by the transformed host cell; (d) treating the serine hydroxymethylase, the phosphoribosylglycinamide formyltransferase, the phosphoribosylaminoimidazolecarboxamide formyltransferase, the formate—tetrahydrofolate ligase or the aminomethyltransferase with a compound to be tested; and (e) comparing the activity of the serine hydroxymethylase, the phosphoribosylglycinamide formyltransferase, the phosphoribosylaminoimidazolecarboxamide formyltransferase, the formate—tetrahydrofolate ligase or the aminomethyltransferase that has been treated with a test compound to the activity of an untreated serine hydroxymethylase, phosphoribosylglycinamide formyltransferase, phosphoribosylaminoimidazolecarboxamide formyltransferase, formate—tetrahydrofolate ligase or aminomethyltransferase, thereby selecting compounds with potential for inhibitory activity.

The present invention relates to a composition, such as a hybridization mixture, comprising an isolated polynucleotide or polypeptide of the present invention.

The present invention relates to an isolated polynucleotide of the present invention comprising at least 30 contiguous nucleotides derived from a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, and 69.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the serine hydroxymethylase, the phosphoribosylglycinamide formyltransferase, the phosphoribosylaminoimidazolecarboxamide formyltransferase, the formate—tetrahydrofolate ligase or the aminomethyltransferase polynucleotide in an amount sufficient to complement a null mutant to provide a positive selection means.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Tetrahydrofolate Metabolic Enzymes

| | | SEQ ID NO: | |
|---|---|---|---|
| Protein | Clone Designation | (Nucleotide) | (Amino Acid) |
| Corn Serine Hydroxymethylase | cr1n.pk0160.h1 | 1 | 2 |
| Rice Serine Hydroxymethylase | rlr72.pk0003.e3 | 3 | 4 |
| Soybean Serine Hydroxymethylase | sfl1.pk125.g5 | 5 | 6 |
| Wheat Serine Hydroxymethylase | Contig of: | 7 | 8 |

TABLE 1-continued

Tetrahydrofolate Metabolic Enzymes

| Protein | Clone Designation | SEQ ID NO: (Nucleotide) | SEQ ID NO: (Amino Acid) |
|---|---|---|---|
| | wlk8.pk0011.e10 | | |
| | wlm96.pk044.f15 | | |
| Corn Serine Hydroxymethylase | p0116.cesar94r | 33 | 34 |
| Rice Serine Hydroxymethylase | rlr72.pk0003.e3:fis | 35 | 36 |
| Soybean Serine Hydroxymethylase | sfl1.pk125.g5:fis | 37 | 38 |
| Wheat Serine Hydroxymethylase | wlk8.pk0011.e10:fis | 39 | 40 |
| Corn Phosphoribosylglycinamide formyltransferase | cco1n.pk058.k22 | 9 | 10 |
| Wheat Phosphoribosylglycinamide formyltransferase | wre1n.pk174.a10 | 11 | 12 |
| Corn Phosphoribosylglycinamide formyltransferase | cco1n.pk058.k22:fis | 41 | 42 |
| Rice Phosphoribosylglycinamide formyltransferase | rca1n.pk004.e20 | 43 | 44 |
| Wheat Phosphoribosylglycinamide formyltransferase | wre1n.pk174.a10:fis | 45 | 46 |
| Rice AICAR Transformylase | r10n.pk081.c17 | 13 | 14 |
| Wheat AICAR Transformylase | wlmk8.pk0015.h6 | 15 | 16 |
| Corn AICAR Transformylase | p0037.crwaf77r | 47 | 48 |
| Rice AICAR Transformylase | r10n.pk081.c17:fis | 49 | 50 |
| Soybean AICAR Transformylase | srn1c.pk002.j23 | 51 | 52 |
| Wheat AICAR Transformylase | wlmk8.pk0015.h6:fis | 53 | 54 |
| Corn Formate--Tetrahydrofolate Ligase | cr1.pk0010.b5 | 17 | 18 |
| Rice Formate--Tetrahydrofolate Ligase | r10n.pk085.h13 | 19 | 20 |
| oybean Formate--Tetrahydrofolate Ligase | ses9c.pk001.p2 | 21 | 22 |
| Wheat Formate--Tetrahydrofolate Ligase | wlmk1.pk0034.f9 | 23 | 24 |
| Corn Formate--Tetrahydrofolate Ligase | Contig of: cr1.pk0010.b5:fis p0030.cdbag33r p0125.czaac39r | 55 | 56 |
| Rice Formate--Tetrahydrofolate Ligase | r10n.pk085.h13:fis | 57 | 58 |
| Soybean Formate--Tetrahydrofolate Ligase | ses9c.pk001.p2:fis | 59 | 60 |
| Wheat Formate--Tetrahydrofolate Ligase | wlmk1.pk0034.f9:fis | 61 | 62 |
| Corn Aminomethyltransferase | ctn1c.pk001.d9 | 25 | 26 |
| Rice Aminomethyltransferase | rlr2.pk0017.b2 | 27 | 28 |
| Soybean Aminomethyltransferase | sgs4c.pk005.p8 | 29 | 30 |
| Wheat Aminomethyltransferase | wl1n.pk0105.h9 | 31 | 32 |
| Corn Aminomethyltransferase | csc1c.pk005.n13 | 63 | 64 |
| Rice Aminomethyltransferase | rlr6.pk0094.f10 | 65 | 66 |
| Soybean Aminomethyltransferase | sgs4c.pk005.p8:fis | 67 | 68 |
| Wheat Aminomethyltransferase | wl1n.pk0105.h9:fis | 69 | 70 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least 40 contiguous nucleotides, most preferably at least 30 contiguous nucleotides derived from SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69 and the complement of such nucleotide sequences may be used in methods of selecting an isolated polynucleotide that affects the expression of a tetrahydrofolate metabolic enzyme polypeptide, such as a serine hydroxymethylase, a phosphoribosylglycinamide formyltransferase, a phosphoribosylaminoimidazolecarboxamide formyltransferase, a formate—tetrahydrofolate ligase or an aminomethyltransferase, in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several tetrahydrofolate metabolic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other serine hydroxymethylases, phosphoribosylglycinamide formyltransferases, phosphoribosylaminoimidazole-carboxamide formyltransferases, formate—tetrahydrofolate ligases or aminomethyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a tetrahydrofolate metabolic enzyme polypeptide of a gene (such as serine hydroxymethylase, phosphoribosylglycinamide formyltransferase, phosphoribosylaminoimidazole-carboxamide formyltransferase, formate—tetrahydrofolate ligase or aminomethyltransferase) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and the complement of such nucleotide sequences; and amplifying a nucleic acid fragment (preferably a cDNA inserted in a cloning vector) using the oligonucleotide primer. The amplified nucleic acid fragment preferably will encode a portion of a tetrahydrofolate metabolic enzyme polypeptide such as serine hydroxymethylase, phosphoribosylglycinamide formyltransferase, phosphoribosylaminoimidazole-carboxamide formyltransferase, formate—tetrahydrofolate ligase or aminomethyltransferase.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of tetrahydrofolate in those cells. Because these enzymes are involved in tetrahydrofolate metabolism, amino acid synthesis, fatty acid biosynthesis and de novo synthesis of purines, inhibition of their activity may be lethal, thus suggesting that they would be attractive herbicide targets. Production of these plant enzymes in bacteria for use in a high throughput screen for chemical inhibitors would be desirable. Alternatively, overproduction of these enzymes in transgenic plants could be used to enhance the production of many secondary metabolites, amino acids, purine nucleic acids and vitamins. Accordingly, the availability of nucleic acid sequences encoding all or a portion of an enzyme involved in tetrahydrofolate metabolism would facilitate studies to better understand tetrahydrofolate metabolism in plants and provide genetic tools to enhance the production of secondary metabolites, amino acids and vitamins. These enzymes may also provide targets to facilitate design and/or identification of inhibitors of tetrahydrofolate metabolism that may be useful as herbicides.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3'0 Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) *Cell*

56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or anti sense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded tetrahydrofolate metabolic enzyme. An example of a vector for high level expression of the instant polypeptides in a bacterial host is provided (Example 10).

Additionally, the instant polypeptides can be used as targets to facilitate design and/or identification of inhibitors of those enzymes that may be useful as herbicides. This is desirable because the polypeptides described herein catalyze various steps in tetrahydrofolate metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cco1n | Corn Cob of 67 Day Old Plants Grown in Green House* | cco1n.pk058.k22 |
| cr1 | Corn Root From 7 Day Old Seedlings | cr1.pk0010.b5 |
| cr1n | Corn Root From 7 Day Old Seedlings* | cr1n.pk0160.h1 |
| csc1c | Corn 20-Day Seedling (Germination Cold Stress). The Seedling Appeared Purple | csc1c.pk005.n13 |
| ctn1c | Corn Tassel, Night Harvested | ctn1c.pk001.d9 |
| p0030 | Corn Endosperm 15 Days After Pollination | p0030.cdbag33r |
| p0037 | Corn V5 Stage** Roots Infested With Corn Root Worm | p0037.crwaf77r |
| p0116 | DAM Methylase-Induced Transgenic BMS Suspension Cells* | p0116.cesar94r |
| p0125 | Corn Anther Prophase I* | p0125.czaac39r |
| rca1n | Rice Callus* | rca1n.pk004.e20 |
| rl0n | Rice 15 Day Old Leaf* | rl0n.pk081.c17 |
| rl0n | Rice 15 Day Old Leaf* | rl0n.pk085.h13 |
| rlr2 | Rice Leaf 15 Days After Germination, 2 Hours After Infection of Strain *Magaporthe grisea* 4360-R-62 (AV2-YAMO); Resistant | rlr2.pk0017.b2 |
| rlr6 | Rice Leaf 15 Days After Germination, 6 Hours After Infection of Strain *Magaporthe grisea* 4360-R-62 (AVR2-YAMO); Resistant | rlr6.pk0094.f10 |
| rlr72 | Rice Leaf 15 Days After Germination, 72 Hours After Infection of Strain *Magaporthe grisea* 4360-R-62 (AVR2-YAMO); Resistant | rlr72.pk0003.e3 |
| ses9c | Soybean Embryogenic Suspension | ses9c.pk001.p2 |
| sfl1 | Soybean Immature Flower | sfl1.pk125.g5 |
| sgc4c | Soybean Cotyledon 14–21 Days After Germination (1/4 yellow) | sgs4c.pk005.p8 |
| srn1c | Soybean Developing Root Nodules | srn1c.pk002.j23 |
| wl1n | Wheat Leaf From 7 Day Old Seedling* | wl1n.pk0105.h9 |
| wlk8 | Wheat Seedlings 8 Hours After Treatment With KQ926** | wlk8.pk0011.e10 |

TABLE 2-continued cDNA Libraries from Corn, Rice, Soybean, and Wheat

| Library | Tissue | Clone |
| --- | --- | --- |
| wlm96 | Wheat Seedlings 96 Hours After Inoculation With *Erysiphe graminis f.* sp *tritici* | wlm96.pk044.f15 |
| wlmk1 | Wheat Seedlings 1 Hour After Inoculation With *Erysiphe graminis f.* sp *tritici* and Treatment With Herbicide** KQ926 | wlmk1.pk0034.f9 |
| wlmk8 | Wheat Seedlings 8 Hours After Inoculation With *Erysiphe graminis f.* sp *tritici* and Treatment With Herbicide** KQ926 | wlmk8.pk0015.h6 |
| wre1n | Wheat Root From 7 Day Old Etiolated Seedling* | wre1n.pk174.a10 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding tetrahydrofolate metabolic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Serine Hydroxymethylase

The BLASTX search using the nucleotide sequences from clones listed in Table 3 revealed similarity of the polypeptides encoded by the cDNAs to serine hydroxymethylases from *Solanum tuberosum* (NCBI General Identifier No. 1707998) or *Pisum sativum* (NCBI General Identifier No. 462187), or to the polypeptide encoded by the contig to serine hydroxymethylase from *Flaveria pringlei* (NCBI General Identifier No. 1346155). Shown in Table 3 are the BLAST results for individual ESTs ("EST"), or the sequences contigs assembled from two ESTs ("Contig"):

TABLE 3

BLAST Results for Sequences Encoding Polypeptides Homologous to Serine Hydroxymethylase

| Clone | Status | NCBI General Identifier No. | BLAST pLog Score |
| --- | --- | --- | --- |
| cr1n.pk0160.h1 | EST | 1707998 | 111.00 |
| r1r72.pk0003.e3 | EST | 1707998 | 61.15 |
| sfl1.pk125.g5 | EST | 462187 | 85.70 |
| Contig of: wlk8.pk0011.e10 wlm96.k044.f15 | Contig | 1346155 | 98.70 |

The sequence of the entire cDNA insert in clones rlr72.pk0003.e3, sfl1.pk125.g5, and wlk8.pk0011.e10 was determined. The bacteria containing clone cr1n.pk0160.h1 did not grow, so another corn clone encoding serine hydroxymethylase was found in the DuPont proprietary database. The BLASTX search using the EST sequences from clone p0116.cesar94r and the BLASTP search using the amino acid sequences from clones rlr72.pk0003.e3:fis, sfl1.pk125.g5:fis, and wlk8.pk0011.e10:fis revealed similarity of the polypeptides encoded by the cDNAs to serine hydroxymethylases from *Solanum tuberosum* (NCBI General Identifier No. 1707998) or *Pisum sativum* (NCBI General Identifier No. 462187), or to the polypeptide encoded by the contig to serine hydroxymethylase from *Flaveria pringlei* (NCBI General Identifier No. 1346155). Shown in Table 4 are the BLAST results for individual ESTs ("EST"), amino acid sequence encoded by the sequences of the entire cDNA inserts comprising the indicated eDNA clones ("FIS"), or the amino acid sequence encoded by the FIS and corresponding to an entire protein ("CGS"):

TABLE 4

BLAST Results for Sequences Encoding Polypeptides Homologous to Serine Hydroxymethylase

| Clone | Status | NCBI General Identifier No. | BLAST pLog Score |
|---|---|---|---|
| p0116.cesar94r | EST | 1707998 | 43.52 |
| rlr72.pk0003.e3:fis | CGS | 1707998 | >254.00 |
| sfl1.pk125.g5:fis | FIS | 462187 | >254.00 |
| wlk8.pk0011.e10:fis | CGS | 1346155 | >254.00 |

The data in Table 5 represents a calculation of the percent identity of the amino acid sequences set forth in SEQ ID NOs:2, 4, 6, 8, 34, 36, 38, and 40 and the *Solanum tuberosum* and *Pisum sativum* sequences (NCBI General Identifier No. 1707998 and 462187, respectively).

TABLE 5

Percent Identity of Amino Acid Sequences Deduced From the Nucleotide Sequences of cDNA Clones Encoding Polypeptides Homologous to Serine Hydroxymethylase

| | Percent Identity to | |
|---|---|---|
| SEQ ID NO. | 1707998 | 462187 |
| 2 | 89.4 | 85.6 |
| 4 | 91.5 | 86.8 |
| 6 | 88.2 | 87.4 |
| 8 | 90.2 | 90.2 |
| 34 | 57.9 | 54.1 |
| 36 | 87.9 | 84.8 |
| 38 | 84.1 | 85.4 |
| 40 | 84.5 | 85.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode substantial portions of corn, rice, soybean, and wheat, an almost entire soybean, an entire rice, and an entire wheat serine hydroxymethylase. These sequences represent the first corn, rice, soybean, and, wheat sequences encoding serine hydroxymethylase.

Example 4

Characterization of cDNA Clones Encoding Phosphoribosylglycinamide Formyltransferase The BLASTX search using the EST sequences from clones listed in Table 6 revealed similarity of the polypeptides encoded by the eDNAs to phosphoribosylglycinamide formyltransferase from *Vigna unguiculata* or *Arabidopsis thaliana* (NCBI General Identifier Nos. 1709923 and 1709922, respectively). Shown in Table 6 are the BLAST results for individual ESTs ("EST"):

TABLE 6

BLAST Results for Sequences Encoding Polypeptides Homologous to Phosphoribosylglycinamide Formyltransferase

| Clone | Status | NCBI General Identifier No. | BLAST pLog Score |
|---|---|---|---|
| cco1n.pk058.k22 | EST | 1709923 | 40.40 |
| wre1n.pk174.a10 | Contig | 1709922 | 27.00 |

The sequence of the entire cDNA insert in the clones mentioned above was determined and further sequencing and searching of the DuPont proprietary database allowed the identification of a rice clone which encodes a protein with similarities to phosphoribosylglycinamide formyltransferase. The BLAST search using the sequences from clones listed in Table 7 revealed similarity of the polypeptides encoded by the cDNAs to phosphoribosylglycinamide formyltransferase from *Vigna unguiculata* (NCBI General Identifier Nos. 1709923)or the polypeptides encoded by the contig to phosphoribosylglycinamide formyltransferase from *Arabidopsis thaliana* (NCBI General Identifier No. 2245095). Shown in Table 7 are the BLAST results for individual ESTs ("EST"), or for the sequences of the entire cDNA inserts comprising the indicated cDNA clones ("FIS"):

TABLE 7

BLAST Results for Sequences Encoding Polypeptides Homologous to Phosphoribosylglycinamide Formyltransferase

| Clone | Status | NCBI General Identifier No. | BLAST pLog Score |
|---|---|---|---|
| cco1n.pk058.k22:fis | FIS | 1709923 | 54.70 |
| rca1n.pk004.e20 | EST | 2245095 | 57.40 |
| wre1n.pk174.a10:fis | FIS* | 1709923 | 87.52 |

*This sequence encodes the mature protein minus the chloroplast transit peptide, it may be called a complete gene sequence.

The data in Table 8 represents a calculation of the percent identity of the amino acid sequences set forth in SEQ ID NOs:10, 12, 42, 44, and 46 and the *Vigna unguiculata* sequence (NCBI General Identifier Nos. 1709923).

TABLE 8

Percent Identity of Amino Acid Sequences Deduced From the Nucleotide Sequences of cDNA Clones Encoding Polypeptides Homologous to Phosphoribosylglycinamide Formyltransferase

| | Percent Identity to |
|---|---|
| SEQ ID NO. | 1709923 |
| 10 | 78.6 |
| 12 | 57.9 |
| 42 | 75.9 |
| 44 | 24.2 |
| 46 | 70.8 |

Sequence alignments and percent identity calculations were performed using the Megalign program of the LASERGENE bioinformatics computing suite (DNASTAR Inc., Multiple alignment of the sequences was performed using the Clustal Madison, Wis.). Multiple alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portions of corn, rice, and wheat phosphoribosylglycinamide formyltransferase. These sequences represent the first corn, rice, and wheat sequences encoding phosphoribosylglycinamide formyltransferase.

Example 5

Characterization of cDNA Clones Encoding Phosphoribosylaminoimidazolecarboxamide Formyltransferase The BLASTX search using the EST sequences from clones listed in Table 9 revealed similarity of the polypeptides encoded by the cDNAs to hosphoribosylaminoimidazoleformyltransferase from *Bacillus cereus* or *Haemophilus influenzae* (NCBI General Identifier No. 2072373 and 1172763, respectively). Shown in Table 9 are the BLAST results for individual ESTs ("EST"):

TABLE 9

BLAST Results for Sequences Encoding Polypeptides Homologous to Phosphoribosylaminoimidazolecarboxamide Formyltransferase

| Clone | Status | NCBI General Identifier No. | BLAST pLog Score |
|---|---|---|---|
| r10n.pk081.c17 | EST | 2072373 | 19.15 |
| wlmk8.pk0015.h6 | EST | 1172763 | 25.30 |

The sequence of the entire cDNA insert in the clones mentioned above was determined and further sequencing of the DuPont proprietary database allowed the identification of corn and soybean clones encoding proteins with similarities to phosphoribosylaminoimidazole-carboxamide formyltransferase. The BLAST search using the sequences from clones listed in Table 10 revealed similarity of the polypeptides encoded by the contig to phosphoribosylaminoimidazole-carboxamide formyltransferase from *Arabidopsis thaliana* (NCBI General Identifier No. 3033398) and to the cDNAs to phosphoribosylaminoimidazole-carboxamide formyltransferase from *Bacillus subtilis* (NCBI General Identifier No. 131638). Shown in Table 10 are the BLAST results for individual ESTs ("EST"), or the sequences of the entire cDNA inserts comprising the indicated cDNA clones ("FIS"):

TABLE 10

BLAST Results for Sequences Encoding Polypeptides Homologous to Phosphoribosylaminoimidazolecarboxamide Formyltransferase

| | | BLAST pLog Score | |
|---|---|---|---|
| Clone | Status | 3033398 | 131638 |
| p0037.crwaf77r | EST | 73.00 | 45.30 |
| r10n.pk081.c17:fis | FIS | >254.00 | 92.10 |
| srn1c.pk002.j23 | EST | 39.70 | 17.70 |
| wlmk8.pk0015.h6:fis | FIS | 133.00 | 57.04 |

The data in Table 11 represents a calculation of the percent identity of the amino acid sequences set forth in SEQ ID NOs:14, 16, 48, 50, 52, and 54 and the *Arabidopsis thaliana* and *Bacillus subtilis* sequences (NCBI General Identifier Nos. 3033398 and 131638, respectively).

TABLE 11

Percent Identity of Amino Acid Sequences Deduced From the Nucleotide Sequences of cDNA Clones Encoding Polypeptides Homologous to Phosphoribosylaminoimidazolecarboxamide Formyltransferase

| | Percent Identity to | |
|---|---|---|
| SEQ ID NO. | 3033398 | 131638 |
| 14 | 75.5 | 43.6 |
| 16 | 90.0 | 47.1 |
| 48 | 41.8 | 29.9 |
| 50 | 78.1 | 37.1 |
| 52 | 88.3 | 53.2 |
| 54 | 80.3 | 35.2 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of corn, rice, soybean, and wheat phosphoribosylaminoimidazole-carboxamide formyltransferase. These sequences represent the first corn, rice, soybean, and wheat sequences encoding phosphoribosylaminoimidazole-carboxamide formyltransferase.

Example 6

Characterization of cDNA Clones Encoding Formate—Tetrahydrofolate Ligase

The BLASTX search using the EST sequences from clones listed in Table 12 revealed similarity of the polypeptides encoded by the cDNAs to formate-tetrahydrofolate ligase from *Spinacia oleracea* (NCBI General Identifier No. 2507455). Shown in Table 12 are the BLAST results for individual ESTs ("EST"):

TABLE 12

BLAST Results for Sequences Encoding Polypeptides Homologous to Formate--Tetrahydrofolate Ligase

| Clone | Status | BLAST pLog Score 2507455 |
|---|---|---|
| cr1.pk0010.b5 | EST | 50.15 |
| r10n.pk085.h13 | EST | 45.00 |
| ses9c.pk001.p2 | EST | 75.00 |
| wlmk1.pk0034.f9 | EST | 57.40 |

The sequence of the entire cDNA insert in the clones listed above was determined. Because the corn clone encodes only a small portion of the C-terminus of the enzyme, the DuPont proprietary database was searched and other clones found to construct a contig which codes for a larger portion of the protein. The BLAST search using the sequences from clones listed in Table 13 revealed similarity of the polypeptides encoded by the cDNAs to formate-tetrahydrofolate ligase from *Arabidopsis thaliana* and *Spinacia oleracea* (NCBI General Identifier Nos. 5921663 and 2507455, respectively). Shown in Table 13 are the BLAST results for the sequences of the entire cDNA inserts comprising the indicated cDNA clones ("FIS"), or a contig assembled from an FIS and two ESTs ("Contig*"):

TABLE 13

BLAST Results for Sequences Encoding Polypeptides Homologous to Formate--Tetrahydrofolate Ligase

| | | BLAST pLog Score | |
|---|---|---|---|
| Clone | Status | 5921663 | 2507455 |
| Contig of:<br>cr1.pk0010.b5:fis<br>p0030.cdbag33r<br>p0125.czaac39r | Contig* | 133.00 | 145.00 |
| r10n.pk085.h13:fis | FIS | 113.00 | 111.00 |
| ses9c.pk001.p2:fis | CGS | >254.00 | >254.00 |
| wlmk1.pk0034.f9:fis | FIS | 129.00 | 127.00 |

The data in Table 14 represents a calculation of the percent identity of the amino acid sequences set forth in SEQ ID NOs:18, 20, 22, 24, 56, 58, 60, and 62 and the *Arabidopsis thaliana* and *Spinacia oleracea* sequences (NCBI General Identifier Nos. 5921663 and 2507455, respectively).

TABLE 14

Percent Identity of Amino Acid Sequences Deduced From the Nucleotide Sequences of cDNA Clones Encoding Polypeptides Homologous to Formate--Tetrahydrofolate Ligase

| | Percent Identity to | |
|---|---|---|
| SEQ ID NO. | 5921663 | 2507455 |
| 18 | 63.9 | 68.9 |
| 20 | 79.8 | 77.7 |
| 22 | 86.6 | 86.6 |
| 24 | 82.7 | 80.8 |
| 56 | 81.5 | 82.2 |
| 58 | 80.8 | 79.1 |
| 60 | 87.3 | 89.6 |
| 62 | 83.2 | 81.7 |

Sequence alignments and percent identity calculations were performed using the Megallign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode substantial portions of a corn, a rice, a soybean, and a wheat and an entire soybean formate-tetrahydrofolate ligase. These sequences represent the first soybean and monocot sequences encoding formate-tetrahydrofolate ligase.

Example 7

Characterization of cDNA Clones Encoding Aminomethyltransferase

The BLASTX search using the EST sequences from clones listed in Table 15 revealed similarity of the polypeptides encoded by the cDNAs to aminomethyltransferase from *Flaveria anomala, Pisum sativum,* or *Solanum tuberosum* (NCBI General Identifier Nos. 3334197, 1346123, and 1707878, respectively). Shown in Table 15 are the BLAST results for individual ESTs ("EST"):

TABLE 15

BLAST Results for Sequences Encoding Polypeptides Homologous to Aminomethyltransferase

| Clone | Status | NCBI General Identifier No. | BLAST pLog Score |
|---|---|---|---|
| ctn1c.pk001.d9 | EST | 3334197 | 42.00 |
| rlr2.pk0017.b2 | EST | 1346123 | 47.00 |
| sgs4c.pk005.p8 | EST | 1707878 | 79.05 |
| wl1n.pk0105.h9 | EST | 1346123 | 44.70 |

The sequence of the entire cDNA insert in clones sgs4c.pk005.pg and wl1n.pk0105.h9 was determined. Different corn and rice clones were identified in the DuPont proprietary database since it was impossible to determine the sequence of the entire cDNA insert in clones ctn1c.pk001.d9 and r1r2.pk0017.b2. The BLAST search using the sequences from clones listed in Table 16 revealed similarity of the polypeptides encoded by the cDNAs to aminomethyltransferase from *Flaveria pringlei, Pisum sativum,* and *Mesembryanthemum crystallinum* (NCBI General Identifier Nos. 1346121, 3915699, and 3334202, respectively) and the contig to aminomethyltransferase from *Mesembryanthemum crystallinum* (NCBI General Identifier No. 3157944). Shown in Table 16 are the BLAST results for individual ESTs ("EST"), or for the sequences of the entire cDNA inserts comprising the indicated cDNA clones and encoding the entire protein ("CGS"):

TABLE 16

BLAST Results for Sequences Encoding Polypeptides Homologous to Aminomethyltransferase

| | | BLAST pLog Score | | | |
|---|---|---|---|---|---|
| Clone | Status | 1346121 | 3915699 | 3334202 | 3157944 |
| csc1c.pk005.-n13 | EST | 32.00 | 32.52 | 34.00 | 34.40 |
| rlr6.pk0094.f10 | EST | 34.70 | 35.00 | 35.15 | 35.70 |
| sgs4c.pk005.-p8:fis | CGS | >254.00 | >254.00 | >254.00 | >254.00 |
| wl1n.pk0105.-h9:fis | CGS | >254.00 | >254.00 | >254.00 | >254.00 |

The data in Table 17 represents a calculation of the percent identity of the amino acid sequence set forth in SEQ ID NOs:26, 28, 30, 32, 64, 66, 68, and 70 and the *Flaveria prinlei, Pisum sativum,* and *Mesembryanthemum crystallinum* sequence (NCBI General Identifier Nos. 1346121, 3915699, and 3334202, respectively).

TABLE 17

Percent Identity of Amino Acid Sequences Deduced From the Nucleotide Sequences of cDNA Clones Encoding Polypeptides Homologous to Aminomethyltransferase

| SEQ ID NO. | Percent Identity to | | |
|---|---|---|---|
| | 1346121 | 3915699 | 3334202 |
| 26 | 83.1 | 86.2 | 87.7 |
| 28 | 70.1 | 72.9 | 70.1 |
| 30 | 80.3 | 78.9 | 76.8 |
| 32 | 76.7 | 78.9 | 78.9 |
| 64 | 58.1 | 59.0 | 62.9 |
| 66 | 41.5 | 44.7 | 42.8 |
| 68 | 88.0 | 92.6 | 85.5 |
| 70 | 78.6 | 76.3 | 75.3 |

Sequence alignments and percent identity calculations were performed using the Meagalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode substantial portions of corn, rice, soybean, and wheat and entire soybean and wheat aminomethyltransferase. These sequences represent the first corn, rice, soybean, and wheat sequences encoding aminomethyltransferase.

Example 8

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this mediun. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 9

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 11

Evaluating Compounds for Their Ability to Inhibit the Activity of Tetrahydrofolate Metabolic Enzymes The polypeptides described herein may be produced using any number of methods known to those skilled in the art. Such methods include, but are not limited to, expression in bacteria as described in Example 10, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for serine hydroxymethylase are presented by Bourguignon et al (1988) *Biochem. J.* 255:169–178. Assays for phosphoribosylglycinamide formyltransferase are presented by Schnorr et al. (1994) *Plant J.* 6:113–121. Assays for phosphoribosylaminoimidazole-carboxamide formyltransferase are presented by Boger et al. (1997) *Bioorg. Med Chem.* 5:1839–1846. Assays for formate— tetrahydrofolate ligase are presented by Nour and Rabinowitz (1991) *J. Biol. Chem.* 266:18363–18369. Assays for aminomethyltransferase are presented by Freudenberg and Andreesen (1989) *J. Bacteriol.* 171:2209–2215.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide that encodes an aminomethyltransferase polypeptide having a sequence identity of at least 95%, based on the Clustal method of alignment, when compared to a polypeptide selected from the group consisting of SEQ ID NOs:26, 28, 30, 32, 64, 66, 68, and 70.

2. The polynucleotide of claim 1 wherein the polynucleotide encodes a polypeptide selected from the group consisting of SEQ ID NOs:26, 28, 30, 32, 64, 66, 68, and 70.

3. The polynucleotide of claim 1, wherein the polynucleotide comprises a nucleotide sequence selected from the group consisting of SEQ ID NOs:25, 27, 29, 31, 63, 65, 67, and 69.

4. An isolated complement of the polynucleotide of claim 1, wherein (a) the complement and the polynucleotide consist of the same number of nucleotides, and (b) the nucleotide sequences of the complement and the polynucleotide have 100% complementarity.

5. A chimeric gene comprising the polynucleotide of claim 1 operably linked to at least one regulatory sequence.

6. A cell comprising the polynucleotide of claim 1.

7. The cell of claim 6, wherein the cell is selected from the group consisting of a yeast cell, a bacterial cell and a plant cell.

8. A transgenic plant comprising the polynucleotide of claim 1.

9. A virus comprising the polynucleotide of claim 1.

10. A method for transforming a cell comprising introducing into a cell the polynucleotide of claim 1.

11. A method for producing a transgenic plant comprising (a) transforming a plant cell with the polynucleotide of claim 1 and (b) regenerating a plant from the transformed plant cell.

12. A method for evaluating at least one compound for its ability to inhibit the activity of an aminomethyltransferase, the method comprising the steps of:

(a) transforming a host cell with a chimeric gene comprising a polynucleotide of claim 1, operably linked to suitable regulatory sequences;

(b) growing the transformed host cell under conditions that are suitable for expression of the chimeric gene wherein expression of the chimeric gene results in production of an aminomethyltransferase encoded by the operably linked nucleic acid fragment in the transformed host cell;

(c) optionally purifying the aminomethyltransferase expressed by the transformed host cell;

(d) treating the aminomethyltransferase with a compound to be tested;

(e) comparing the activity of the aminomethyltransferase that has been treated with the compound with the activity of an aminomethyltransferase that has not been treated; and (f) selecting compounds with inhibitory activity.

13. An isolated polynucleotide that encodes an aminomethyltransferase polypeptide having a sequence identity of at least 90%, based on the Clustal method of alignment, when compared to a polypeptide selected from the group consisting of SEQ ID NOs:26, 28, 30, 32, 64, 66, and 70.

14. An isolated complement of the polynucleotide of claim 13, wherein (a) the complement and the polynucleotide consist of the same number of nucleotides, and (b) the nucleotide sequences of the complement and the polynucleotide have 100% complementarity.

* * * * *

SEQUENCE LISTING

<160> NUMBER OF SEQ ID NOS: 70

<210> SEQ ID NO 1
<211> LENGTH: 586
<212> TYPE: DNA
<213> ORGANISM: Zea mays
<220> FEATURE:
<221> NAME/KEY: unsure
<222> LOCATION: (584)

<400> SEQUENCE: 1

| | | | | | |
|---|---|---|---|---|---|
| gaaaagcgct | gttcttttta | ggccaaagtt | gatcattgct | ggtgcaagtg | catatgctcg | 60 |
| gctatatgat | tatgaccgta | tgcggaagat | atgcaacaag | cagaaggcaa | tacttctagc | 120 |
| agacatggca | catattagtg | ggcttgttgc | agctggtgtt | gttccatctc | cttttgatta | 180 |
| tgcagatgta | gtgactacca | ctactcacaa | atcactccgt | gggccacgtg | gagccatgat | 240 |
| cttttacagg | aagggagtca | agaaataaa | taaacaagga | aaagaggtta | tgtatgattt | 300 |
| tgaggacaaa | atcaatgctg | ctgtctttcc | tggtctgcaa | ggtgggcctc | ataaccatac | 360 |
| cattactggc | ttggctgttg | cgctcaaaca | ggcaactact | ccagaataca | gagcttacca | 420 |
| agagcaagtt | atcagtaatt | gtgctaaatt | tgcgcagagc | ctgatttcaa | aaggatatga | 480 |
| actcgtctct | ggtgggactg | acaaccattt | agttctggtg | aatctcaaga | ataaggggat | 540 |
| agatgttcaa | gggtggagaa | ggtttagaaa | gtgtgcatat | tcanca | | 586 |

<210> SEQ ID NO 2
<211> LENGTH: 180
<212> TYPE: PRT
<213> ORGANISM: Zea mays

<400> SEQUENCE: 2

```
Lys Ser Ala Val Leu Phe Arg Pro Lys Leu Ile Ile Ala Gly Ala Ser
  1               5                  10                  15

Ala Tyr Ala Arg Leu Tyr Asp Tyr Asp Arg Met Arg Lys Ile Cys Asn
             20                  25                  30

Lys Gln Lys Ala Ile Leu Leu Ala Asp Met Ala His Ile Ser Gly Leu
         35                  40                  45

Val Ala Ala Gly Val Val Pro Ser Pro Phe Asp Ala Asp Val Val Thr
     50                  55                  60

Thr Thr Thr His Lys Ser Leu Arg Gly Pro Arg Gly Ala Met Ile Phe
 65                  70                  75                  80

Tyr Arg Lys Gly Val Lys Glu Ile Asn Lys Gln Gly Lys Glu Val Met
                 85                  90                  95

Tyr Asp Phe Glu Asp Lys Ile Asn Ala Ala Val Phe Pro Gly Leu Gln
            100                 105                 110

Gly Gly Pro His Asn His Thr Ile Thr Gly Leu Ala Val Ala Leu Lys
        115                 120                 125

Gln Ala Thr Thr Pro Glu Tyr Arg Ala Tyr Gln Glu Gln Val Ile Ser
    130                 135                 140

Asn Cys Ala Lys Phe Ala Gln Ser Leu Ile Ser Lys Gly Tyr Glu Leu
145                 150                 155                 160

Val Ser Gly Gly Thr Asp Asn His Leu Val Leu Val Asn Leu Lys Asn
                165                 170                 175

Lys Gly Ile Asp
            180
```

<210> SEQ ID NO 3
<211> LENGTH: 476
<212> TYPE: DNA
<213> ORGANISM: Oryza sativa

<400> SEQUENCE: 3

```
tacacacccc cgcctccacc accacccgcc gctcgccgct cgcccaccat ggccatggcg      60
acggcgctcc gcaagctctc ctccgacgcc ctccgccgcc agccgctctc ccgcatcacc     120
ccgtctctact acatggcgtc cctgccggcg acggaggaga gatccggagt cacctggccg    180
aagcagctga acgcgccgct ggaggaggtg gatcccgaga tcgccgacat catcgagcac    240
gagaaggccc gccaatggaa gggtctggag ctcatcccgt cggagaactt cacctcggtg    300
tcagtgatgc aggcggtggg atccgtcatg accaacaagt acagcgaggg gtaccccggc    360
gcgagatact acggtggaaa cgaatacatt gatatggccg agtcattgtg ccagaaacgt    420
gctttggagg cttccgcttg gaacccagcg aaatgggag tgaatgtgca actcta          476
```

<210> SEQ ID NO 4
<211> LENGTH: 106
<212> TYPE: PRT
<213> ORGANISM: Oryza sativa

<400> SEQUENCE: 4

```
Glu Glu Arg Ser Gly Val Thr Trp Pro Lys Gln Leu Asn Ala Pro Leu
  1               5                  10                  15

Glu Glu Val Asp Pro Glu Ile Ala Asp Ile Ile Glu His Glu Lys Ala
             20                  25                  30

Arg Gln Trp Lys Gly Leu Glu Leu Ile Pro Ser Glu Asn Phe Thr Ser
         35                  40                  45

Val Ser Val Met Gln Ala Val Gly Ser Val Met Thr Asn Lys Tyr Ser
     50                  55                  60

Glu Gly Tyr Pro Gly Ala Arg Tyr Tyr Gly Gly Asn Glu Tyr Ile Asp
 65                  70                  75                  80

Met Ala Glu Ser Leu Cys Gln Lys Arg Ala Leu Glu Ala Ser Ala Trp
                 85                  90                  95

Asn Pro Ala Lys Trp Gly Val Asn Val Gln
            100                 105
```

<210> SEQ ID NO 5
<211> LENGTH: 566
<212> TYPE: DNA
<213> ORGANISM: Glycine max
<220> FEATURE:
<221> NAME/KEY: unsure
<222> LOCATION: (451)
<220> FEATURE:
<221> NAME/KEY: unsure
<222> LOCATION: (564)

<400> SEQUENCE: 5

```
ggcaatggca cttggcaggc tttcatcttc cttcaacaag cctttacgtc ctctcttcaa      60
tgctggctca gtttactaca agtcctcttt gcctgctgaa gctgcgtacg acaatgagaa    120
aagctgtgat acgaattga atgctccact tgaggttgtt gatcctgaga ttgctgatat    180
aattgagctt gaaaagcta gacaatggaa gggactggaa ctgatacct cgagaatt      240
cacttctgtc tctgtaatgc aagctattgg ctctatcatt actaacactc ggaatgaagg    300
atatcccggt gcaagatatt atgggggaaa tgagtatatt gacatggcag aaacactatg    360
```

```
tcaaaaacgt gccttggaag catttcggtt ggatccggct aaatggggag tgaacgtgca    420
gcctctgtct gggttcttct gccaatttca ngtttacact gcattgctaa aacctcatga    480
tagaatcatg ggacttgatc taccacatgg aggcatcttt ctcatggata cagactgaca    540
caataaggat ctgcagtctc ctantt                                          566
```

<210> SEQ ID NO 6
<211> LENGTH: 127
<212> TYPE: PRT
<213> ORGANISM: Glycine max
<220> FEATURE:
<221> NAME/KEY: UNSURE
<222> LOCATION: (106)

<400> SEQUENCE: 6

```
Glu Leu Asn Ala Pro Leu Glu Val Val Asp Pro Glu Ile Ala Asp Ile
 1               5                  10                  15

Ile Glu Leu Glu Lys Ala Arg Gln Trp Lys Gly Leu Glu Leu Ile Pro
                20                  25                  30

Ser Glu Asn Phe Thr Ser Val Ser Val Met Gln Ala Ile Gly Ser Ile
            35                  40                  45

Ile Thr Asn Thr Arg Asn Glu Gly Tyr Pro Gly Ala Arg Tyr Tyr Gly
        50                  55                  60

Gly Asn Glu Tyr Ile Asp Met Ala Glu Thr Leu Cys Gln Lys Arg Ala
 65                  70                  75                  80

Leu Glu Ala Phe Arg Leu Asp Pro Ala Lys Trp Gly Val Asn Val Gln
                85                  90                  95

Pro Leu Ser Gly Phe Phe Cys Gln Phe Xaa Val Tyr Thr Ala Leu Leu
           100                 105                 110

Lys Pro His Asp Arg Ile Met Gly Leu Asp Leu Pro His Gly Gly
           115                 120                 125
```

<210> SEQ ID NO 7
<211> LENGTH: 792
<212> TYPE: DNA
<213> ORGANISM: Triticum aestivum
<220> FEATURE:
<221> NAME/KEY: unsure
<222> LOCATION: (697)
<220> FEATURE:
<221> NAME/KEY: unsure
<222> LOCATION: (707)
<220> FEATURE:
<221> NAME/KEY: unsure
<222> LOCATION: (720)
<220> FEATURE:
<221> NAME/KEY: unsure
<222> LOCATION: (758)..(759)
<220> FEATURE:
<221> NAME/KEY: unsure
<222> LOCATION: (763)
<220> FEATURE:
<221> NAME/KEY: unsure
<222> LOCATION: (792)

<400> SEQUENCE: 7

```
ctcgtgccga attcggcacg agcctaccga gaggtgcacg aggaggccgc ccaccaccac    60
cacccaccat ggccatggcg acggcgctcc gcaagctctc cgcccgcggc cagcccctct   120
cccgcctcac gccgctctac tccatggcgt ccctgccggc gacggaggag agatccgcag   180
tcacctggcc gaagcagttg aacgcgccgc tggaggaggt cgaccccgag attgccgaca   240
tcatcgagct cgagaaggcc cgccaatgga agggctgga gctcatcccg tcggagaact   300
```

```
tcacctccct gtcggtgatg caggcggtgg gatccgtcat gaccaacaag tacagcgagg    360
ggtaccccgg cgcgagatac tacggtggaa acgaatacat tgatatggcc gagacgctgt    420
gtcagaaacg tgctttggag gccttcaatt tggacccgga agtgggga gtgaatgtgc      480 aacctctatc gggttcacct gccaacttcc atgtatacac tgctctgctg aagccacatg    540
acagaattat ggctctggat cttcctcacg gtggacatct ttcccatggt taccaagact    600
gacacaaaga aaatctcagc aagtttcaat attctttgag acaatgcctt acagaccggg    660
atgaaagcac tggcttgatt gattatgacc agttggngaa aaagtgncgt tcctgtttan    720
gccaaaagtt gattgtttgc tggggctagt gcaaaatnnc ccnccttaa ttattattac     780 cgcaatgcgg gn                                                         792
```

<210> SEQ ID NO 8
<211> LENGTH: 163
<212> TYPE: PRT
<213> ORGANISM: Triticum aestivum

<400> SEQUENCE: 8

```
Glu Glu Arg Ser Ala Val Thr Trp Pro Lys Gln Leu Asn Ala Pro Leu
 1               5                  10                  15

Glu Glu Val Asp Pro Glu Ile Ala Asp Ile Ile Glu Leu Glu Lys Ala
             20                  25                  30

Arg Gln Trp Lys Gly Leu Glu Leu Ile Pro Ser Glu Asn Phe Thr Ser
         35                  40                  45

Leu Ser Val Met Gln Ala Val Gly Ser Val Met Thr Asn Lys Tyr Ser
     50                  55                  60

Glu Gly Tyr Pro Gly Ala Arg Tyr Tyr Gly Asn Glu Tyr Ile Asp
 65                  70                  75                  80

Met Ala Glu Thr Leu Cys Gln Lys Arg Ala Leu Glu Ala Phe Asn Leu
                 85                  90                  95

Asp Pro Glu Lys Trp Gly Val Asn Val Gln Pro Leu Ser Gly Ser Pro
            100                 105                 110

Ala Asn Phe His Val Tyr Thr Ala Leu Leu Lys Pro His Asp Arg Ile
        115                 120                 125

Met Ala Leu Asp Leu Pro His Gly Gly His Leu Ser His Gly Tyr Lys
    130                 135                 140

Thr Asp Thr Arg Lys Ser Gln Gln Val Ser Ile Phe Phe Glu Thr Met
145                 150                 155                 160

Pro Tyr Arg
```

<210> SEQ ID NO 9
<211> LENGTH: 523
<212> TYPE: DNA
<213> ORGANISM: Zea mays
<220> FEATURE:
<221> NAME/KEY: unsure
<222> LOCATION: (15)

<400> SEQUENCE: 9

```
aaagctgtta ttgcntctgg agcaagatac tcgggtccaa ccgtacattt tgtggatgag     60
cactatgata ccgtaaaaac gttagcccag agggttgtgc ctgtgttcgc ggatgacacg    120
ccagagctat ggctgcaag agtcctccat gaggaacata tggtctatgt tgaagcagtt    180
gctgctttgt gcgaggaccg cgtcgtatgg agggaagatg tgtcccact tatcaaaagt    240 cggacaaatc cagctgtgta catctaattg acaatacggc aatagtagca ctattttgga    300
```

```
gtaataatgg aatttgtaga gcccttgcca cttttcccgg taaaaggggt acttagcagt    360
tgacgtaggg ttgatataca gggcacaact tatttgccac cgaaacattt ccatgcgttg    420
gaagtgagaa acattgcccc caataggccg cagtatccat tactgcatgg aacaaggttg    480 aaatttttacc ttgatttgag ataactatca aaaaaaaaaa aaa                    523
```

<210> SEQ ID NO 10
<211> LENGTH: 84
<212> TYPE: PRT
<213> ORGANISM: Zea mays

<400> SEQUENCE: 10

```
Lys Ala Val Ile Ala Ser Gly Ala Arg Tyr Ser Gly Pro Thr Val His
 1               5                  10                  15

Phe Val Asp Glu His Tyr Asp Thr Gly Lys Thr Leu Ala Gln Arg Val
                20                  25                  30

Val Pro Val Phe Ala Asp Asp Thr Pro Glu Leu Leu Ala Ala Arg Val
            35                  40                  45

Leu His Glu Glu His Met Val Tyr Val Glu Ala Val Ala Ala Leu Cys
        50                  55                  60

Glu Asp Arg Val Val Trp Arg Glu Asp Gly Val Pro Leu Ile Lys Ser
65                  70                  75                  80

Arg Thr Asn Pro
```

<210> SEQ ID NO 11
<211> LENGTH: 407
<212> TYPE: DNA
<213> ORGANISM: Triticum aestivum
<220> FEATURE:
<221> NAME/KEY: unsure
<222> LOCATION: (252)
<220> FEATURE:
<221> NAME/KEY: unsure
<222> LOCATION: (259)
<220> FEATURE:
<221> NAME/KEY: unsure
<222> LOCATION: (271)
<220> FEATURE:
<221> NAME/KEY: unsure
<222> LOCATION: (276)
<220> FEATURE:
<221> NAME/KEY: unsure
<222> LOCATION: (284)..(285)
<220> FEATURE:
<221> NAME/KEY: unsure
<222> LOCATION: (307)
<220> FEATURE:
<221> NAME/KEY: unsure
<222> LOCATION: (329)
<220> FEATURE:
<221> NAME/KEY: unsure
<222> LOCATION: (332)
<220> FEATURE:
<221> NAME/KEY: unsure
<222> LOCATION: (354)
<220> FEATURE:
<221> NAME/KEY: unsure
<222> LOCATION: (396)
<220> FEATURE:
<221> NAME/KEY: unsure
<222> LOCATION: (403)

<400> SEQUENCE: 11

```
agaggctcgc ggtgttcgtc tcaggcgggg gctcgaactt ccggtcgatc cacgaggccg    60
ttctgggtgg gaaggtgaac ggggatgttg ttgcgctcgt caccgataag ccaggctgcg   120
gtggcgcgga gtatgcaagg tgcaatggca tgcccgtggt cgtgtttccc aagtcgaaat   180
```

```
cggcgccggg aggggggtctc cacagatgaa cttctgaatg ttctgaggat tctgaaaggt      240
aaactttatt cnacttgcng gttacttgaa ncccanacct ggtnncctat ttagtcaatt      300
tcccaanttc aagcctaaat aaaaccttna angcccccgg aatttttggag gcanggttat      360 aaggttgaaa tgcctaacaa ttttttgccat ctgggncaaa ccncagg                   407
```

<210> SEQ ID NO 12
<211> LENGTH: 76
<212> TYPE: PRT
<213> ORGANISM: Triticum aestivum

<400> SEQUENCE: 12

```
Arg Leu Ala Val Phe Val Ser Gly Gly Gly Ser Asn Phe Arg Ser Ile
 1               5                  10                  15

His Glu Ala Val Leu Gly Gly Lys Val Asn Gly Asp Val Val Ala Leu
            20                  25                  30

Val Thr Asp Lys Pro Gly Cys Gly Gly Ala Glu Tyr Ala Arg Cys Asn
        35                  40                  45

Gly Met Pro Val Val Phe Pro Lys Ser Lys Ser Ala Pro Gly Glu
    50                  55                  60

Gly Val Ser Thr Asp Glu Leu Leu Asn Val Leu Arg
65                  70                  75
```

<210> SEQ ID NO 13
<211> LENGTH: 358
<212> TYPE: DNA
<213> ORGANISM: Oryza sativa
<220> FEATURE:
<221> NAME/KEY: unsure
<222> LOCATION: (301)
<220> FEATURE:
<221> NAME/KEY: unsure
<222> LOCATION: (356)

<400> SEQUENCE: 13

```
cttacagtga acttgtatcc attctataac aaggtcacct ctggtgtaat ttctttcgag      60
gatggcattg aaaacattga tatcggtgga cctacgatga tccgagcagc agctaagaat     120
cataaggatg ttcttgttat ggtggatcat gaagattacc ctgctctatt agagtatctg     180
caaggaaaac aagatgacca gcaattccgc aagatgctag catggaaagc tttccaacat     240
gtcgcttctt atgattcagc tgtctcagaa tggttgtgga agcaatccga acaaaggaga     300
ngtatccccc ccgaacttaa ccgttgcccc tttccctaaa tccaaacttc cgtttngg       358
```

<210> SEQ ID NO 14
<211> LENGTH: 94
<212> TYPE: PRT
<213> ORGANISM: Oryza sativa

<400> SEQUENCE: 14

```
Val Asn Leu Tyr Pro Phe Tyr Asn Lys Val Thr Ser Gly Val Ile Ser
 1               5                  10                  15

Phe Glu Asp Gly Ile Glu Asn Ile Asp Ile Gly Gly Pro Thr Met Ile
            20                  25                  30

Arg Ala Ala Ala Lys Asn His Lys Asp Val Leu Val Met Val Asp His
        35                  40                  45

Glu Asp Tyr Pro Ala Leu Leu Leu Glu Tyr Leu Gln Gly Lys Gln Asp
    50                  55                  60

Asp Gln Gln Phe Arg Lys Met Leu Ala Trp Lys Ala Phe Gln His Val
```

65                  70                  75                  80
                    Ala Ser Tyr Asp Ser Ala Val Ser Glu Trp Leu Trp Lys Gln
                                              85                  90

<210> SEQ ID NO 15
<211> LENGTH: 616
<212> TYPE: DNA
<213> ORGANISM: Triticum aestivum
<220> FEATURE:
<221> NAME/KEY: unsure
<222> LOCATION: (293)
<220> FEATURE:
<221> NAME/KEY: unsure
<222> LOCATION: (385)
<220> FEATURE:
<221> NAME/KEY: unsure
<222> LOCATION: (409)
<220> FEATURE:
<221> NAME/KEY: unsure
<222> LOCATION: (435)
<220> FEATURE:
<221> NAME/KEY: unsure
<222> LOCATION: (455)
<220> FEATURE:
<221> NAME/KEY: unsure
<222> LOCATION: (514)
<220> FEATURE:
<221> NAME/KEY: unsure
<222> LOCATION: (530)
<220> FEATURE:
<221> NAME/KEY: unsure
<222> LOCATION: (554)
<220> FEATURE:
<221> NAME/KEY: unsure
<222> LOCATION: (561)
<220> FEATURE:
<221> NAME/KEY: unsure
<222> LOCATION: (596)
<220> FEATURE:
<221> NAME/KEY: unsure
<222> LOCATION: (609)

<400> SEQUENCE: 15
cttggatgct gatgctgcat ggaattgtgt gtcagagttt gagaatccta cttgtgttgt      60
ggttaagcac accaatccgt gcggtgttgc atcccggcag gatgttcttg aggcatacag     120
gttggccgta agggcagatc ctgtgagtgc atttggcgga atcgttgcat tcaacaccac     180
agttgacgag gatcttgcaa aggagattcg cgagtttaga agtcctacag atggcgagac     240
tcggatgttc tatgagatcg tggtggcacc aggatacaca gagaagggcc tcnaggtcct     300
caaagggaaa tccaagacgt tgaggatcct tgaggcaaag agaagtgggg aaaacatgct     360
gtcgctcaag caagtcaatg gtggntggct aactcaagat ccgacgatnt aacccaagaa     420
gacatcaact tcacnacggg ttctaaaaaa ctccnacggc atgagctaac ggatgcaaat     480
tccctggtct cctgaacact caagacaacc catntgattg caaggaaatn catctggcat     540
gggacggcac caanaggtgg nacctaggtt ctcaagaaca gggagcccaa ggaacnccgg     600
aaaaacctnt ccatcc                                                     616

<210> SEQ ID NO 16
<211> LENGTH: 70
<212> TYPE: PRT
<213> ORGANISM: Triticum aestivum

<400> SEQUENCE: 16

Asp Ala Asp Ala Ala Trp Asn Cys Val Ser Glu Phe Glu Asn Pro Thr
  1               5                  10                  15

```
Cys Val Val Lys His Thr Asn Pro Cys Gly Val Ala Ser Arg Gln
            20                  25                  30

Asp Val Leu Glu Ala Tyr Arg Leu Ala Val Arg Ala Asp Pro Val Ser
            35                  40                  45

Ala Phe Gly Gly Ile Val Ala Phe Asn Thr Thr Val Asp Glu Asp Leu
        50                  55                  60

Ala Lys Glu Ile Arg Glu
 65                  70

<210> SEQ ID NO 17
<211> LENGTH: 432
<212> TYPE: DNA
<213> ORGANISM: Zea mays
<220> FEATURE:
<221> NAME/KEY: unsure
<222> LOCATION: (213)

<400> SEQUENCE: 17
tcttgctaaa catatatcaa acacgaggag ttatggagtt aatgttgtag ttgcaatcaa      60
caaatttgca tcagatactg aggcagaaat gaaggcagtg cacagtgcag ctatggctgc    120
tggtgctttt gacgctgttg tctgcacaca ccatgcccat ggtggtaaag gagcggttga    180
gcttggactt gctgttcaac gagcatgcga aanccaggca gaacctctga agttttttgta    240 tcccttggaa tctagcataa aggagaagat tgagtcaatt gctaagttct atggtgctag    300
tggcgttgaa tattccgagc aggtgagaag cagattgaga tgtacaccaa gcaagggttc    360
tccagctccc catttgcatg ggaagaccag tactcattct cacatgtccg tcataagggc    420
gcccgaccgg ct                                                        432

<210> SEQ ID NO 18
<211> LENGTH: 119
<212> TYPE: PRT
<213> ORGANISM: Zea mays
<220> FEATURE:
<221> NAME/KEY: UNSURE
<222> LOCATION: (71)

<400> SEQUENCE: 18

Leu Ala Lys His Ile Ser Asn Thr Arg Ser Tyr Gly Val Asn Val Val
 1               5                  10                  15

Val Ala Ile Asn Lys Phe Ala Ser Asp Thr Glu Ala Glu Met Lys Ala
            20                  25                  30

Val His Ser Ala Ala Met Ala Ala Gly Ala Phe Asp Ala Val Val Cys
        35                  40                  45

Thr His His Ala His Gly Gly Lys Gly Ala Val Glu Leu Gly Leu Ala
    50                  55                  60

Val Gln Arg Ala Cys Glu Xaa Gln Ala Glu Pro Leu Lys Phe Leu Tyr
65                  70                  75                  80

Pro Leu Glu Ser Ser Ile Lys Glu Lys Ile Glu Ser Ile Ala Lys Phe
                85                  90                  95

Tyr Gly Ala Ser Gly Val Glu Tyr Ser Glu Gln Val Arg Ser Arg Leu
            100                 105                 110

Arg Cys Thr Pro Ser Lys Gly
        115

<210> SEQ ID NO 19
<211> LENGTH: 542
<212> TYPE: DNA
<213> ORGANISM: Oryza sativa
```

```
<220> FEATURE:
<221> NAME/KEY: unsure
<222> LOCATION: (364)
<220> FEATURE:
<221> NAME/KEY: unsure
<222> LOCATION: (366)
<220> FEATURE:
<221> NAME/KEY: unsure
<222> LOCATION: (379)
<220> FEATURE:
<221> NAME/KEY: unsure
<222> LOCATION: (410)
<220> FEATURE:
<221> NAME/KEY: unsure
<222> LOCATION: (422)
<220> FEATURE:
<221> NAME/KEY: unsure
<222> LOCATION: (426)
<220> FEATURE:
<221> NAME/KEY: unsure
<222> LOCATION: (448)
<220> FEATURE:
<221> NAME/KEY: unsure
<222> LOCATION: (451)
<220> FEATURE:
<221> NAME/KEY: unsure
<222> LOCATION: (464)
<220> FEATURE:
<221> NAME/KEY: unsure
<222> LOCATION: (466)
<220> FEATURE:
<221> NAME/KEY: unsure
<222> LOCATION: (471)
<220> FEATURE:
<221> NAME/KEY: unsure
<222> LOCATION: (485)
<220> FEATURE:
<221> NAME/KEY: unsure
<222> LOCATION: (493)
<220> FEATURE:
<221> NAME/KEY: unsure
<222> LOCATION: (500)
<220> FEATURE:
<221> NAME/KEY: unsure
<222> LOCATION: (525)
<220> FEATURE:
<221> NAME/KEY: unsure
<222> LOCATION: (527)
<220> FEATURE:
<221> NAME/KEY: unsure
<222> LOCATION: (529)
<220> FEATURE:
<221> NAME/KEY: unsure
<222> LOCATION: (535)
<220> FEATURE:
<221> NAME/KEY: unsure
<222> LOCATION: (542)

<400> SEQUENCE: 19
cttacaatta gagctcttaa aatgcatggt gggggccctg atgttgtggc tgggaagcct      60
ttggatcatg catatgtgag tgaaaatgtg gctcttgttg aagctggatg cgtcaatctt    120
gctaaacata tcgcaaacac aaagagttat ggagttaatg ttgtagttgc aatcaacaag    180
tttgcatcag atactgaagc agaaatggac gtggtgcgaa atgcgtcttt ggctgctggt    240
gcttttgatg ctgttgtctg cactcaccat gcgcatggtg gtaaaaggag cgggttgatc    300
tttggactcg cggttcaaac gggcaagttg agagccaagg caagaaccct ctgaaaattt    360
tggnanccct aaaaatccng gcataaaagg agaaagattg agtcaataan ctaagttcca    420
angggnctaa accggcgttt gaataacncc ngaacaaggc gggngnaaac nagattggaa    480
atgtntaaca agncaaaggn ttccaaaacc tcccaaatat ccatngngna aaacncaatt    540 an                                                                  542
```

<210> SEQ ID NO 20
<211> LENGTH: 94
<212> TYPE: PRT
<213> ORGANISM: Oryza sativa

<400> SEQUENCE: 20

Thr Ile Arg Ala Leu Lys Met His Gly Gly Pro Asp Val Val Ala
 1               5                  10                  15

Gly Lys Pro Leu Asp His Ala Tyr Val Ser Glu Asn Val Ala Leu Val
                 20                  25                  30

Glu Ala Gly Cys Val Asn Leu Ala Lys His Ile Ala Asn Thr Lys Ser
             35                  40                  45

Tyr Gly Val Asn Val Val Ala Ile Asn Lys Phe Ala Ser Asp Thr
 50                  55                  60

Glu Ala Glu Met Asp Val Val Arg Asn Ala Ser Leu Ala Ala Gly Ala
 65                  70                  75                  80

Phe Asp Ala Val Val Cys Thr His His Ala His Gly Gly Lys
                 85                  90

<210> SEQ ID NO 21
<211> LENGTH: 550
<212> TYPE: DNA
<213> ORGANISM: Glycine max
<220> FEATURE:
<221> NAME/KEY: unsure
<222> LOCATION: (418)
<220> FEATURE:
<221> NAME/KEY: unsure
<222> LOCATION: (533)

<400> SEQUENCE: 21
ctgaaatctt agtttctgcc cgaaactgaa actgaatcga aattcaatac aatgagttcc      60
tcaactacag tgaggaagtt gcaggtggtg tcccctgttc ctgcggacat agacattgca     120
aactccgttg aacccgttca tatctcccag attgccaaag acctcaacct tagtcccaat     180
cactatgacc tttacggtaa atacaaggct aaggttttgt tgtcggttct tgatgagctt     240
caaggatcag aagatgggta ttatgttgtg gtcggaggca ttactccgac tcctctcggg     300
gaaggcaaat ctactactac agtggggctc tgtcaagctt taggtgcttt tcttgataaa     360
aaggtagtca cctgccttcg tcaaccatcg caaggaccta cttttggaat taaggangt     420 gcaactggtg gtggctatag ccaagttatt cccaagggat gaattcaatc ttcatctaac     480
agggagatat tcatgcaata actgcagcaa acatcctcaa gctgcgcaat tgntacccga     540
attttcatga                                                            550

<210> SEQ ID NO 22
<211> LENGTH: 134
<212> TYPE: PRT
<213> ORGANISM: Glycine max
<220> FEATURE:
<221> NAME/KEY: UNSURE
<222> LOCATION: (121)

<400> SEQUENCE: 22

Ser Ser Thr Thr Val Arg Lys Leu Gln Val Val Ser Pro Val Pro Ala
 1               5                  10                  15

Asp Ile Asp Ile Ala Asn Ser Val Glu Pro Val His Ile Ser Gln Ile
                 20                  25                  30

Ala Lys Asp Leu Asn Leu Ser Pro Asn His Tyr Asp Leu Tyr Gly Lys 35                  40                  45
Tyr Lys Ala Lys Val Leu Leu Ser Val Leu Asp Glu Leu Gln Gly Ser
                    50                  55                  60

Glu Asp Gly Tyr Tyr Val Val Gly Gly Ile Thr Pro Thr Pro Leu
65                  70                  75                  80

Gly Glu Gly Lys Ser Thr Thr Thr Val Gly Leu Cys Gln Ala Leu Gly
                85                  90                  95

Ala Phe Leu Asp Lys Lys Val Val Thr Cys Leu Arg Gln Pro Ser Gln
            100                 105                 110

Gly Pro Thr Phe Gly Ile Lys Gly Xaa Ala Thr Gly Gly Gly Tyr Ser
        115                 120                 125

Gln Val Ile Pro Lys Gly
    130

<210> SEQ ID NO 23
<211> LENGTH: 535
<212> TYPE: DNA
<213> ORGANISM: Triticum aestivum
<220> FEATURE:
<221> NAME/KEY: unsure
<222> LOCATION: (334)
<220> FEATURE:
<221> NAME/KEY: unsure
<222> LOCATION: (371)
<220> FEATURE:
<221> NAME/KEY: unsure
<222> LOCATION: (374)
<220> FEATURE:
<221> NAME/KEY: unsure
<222> LOCATION: (391)
<220> FEATURE:
<221> NAME/KEY: unsure
<222> LOCATION: (408)
<220> FEATURE:
<221> NAME/KEY: unsure
<222> LOCATION: (410)
<220> FEATURE:
<221> NAME/KEY: unsure
<222> LOCATION: (460)
<220> FEATURE:
<221> NAME/KEY: unsure
<222> LOCATION: (468)
<220> FEATURE:
<221> NAME/KEY: unsure
<222> LOCATION: (471)
<220> FEATURE:
<221> NAME/KEY: unsure
<222> LOCATION: (480)
<220> FEATURE:
<221> NAME/KEY: unsure
<222> LOCATION: (506)
<220> FEATURE:
<221> NAME/KEY: unsure
<222> LOCATION: (522)
<220> FEATURE:
<221> NAME/KEY: unsure
<222> LOCATION: (533)..(534)

<400> SEQUENCE: 23
gggactgaga aattcatgga cataaagtgt aggtatagtg gattgacacc tcagtgtgct     60
attattgtgg ccacaattag ggctcttaaa atgcatggag gaggcccaga tgttgtggct    120
gggaagcctt tagatcatgc atatgtcagt gaaaatgtgg ctcttgttga agctggatgt    180
gttaatcttg ctaagcacat ctcaaacaca aagggttatg gagtgaatgt tgtagtagca    240
atcaacaaat ttgcaacaga cacagacgct gaaatggaag ttgtgaaaaa ggcggctatg    300
gcagctgggg cttccatgct gcgtctgctc ccancatgca cacggtggta aaggagcgtt    360

-continued

```
tatcttggga nccnctgttc aaaagacatt naaagcaagc aaggcccngn agttttaaat     420
ccttagatcc aacataaaag agaaattgat ccatactaan tctaaggngc naatgggttn     480
aatacccgaa caagcgaaaa caaatnagat ttcacaacaa gntctcaact ccnng          535
```

<210> SEQ ID NO 24
<211> LENGTH: 104
<212> TYPE: PRT
<213> ORGANISM: Triticum aestivum

<400> SEQUENCE: 24

```
Gly Thr Glu Lys Phe Met Asp Ile Lys Cys Arg Tyr Ser Gly Leu Thr
  1               5                  10                  15

Pro Gln Cys Ala Ile Ile Val Ala Thr Ile Arg Ala Leu Lys Met His
             20                  25                  30

Gly Gly Gly Pro Asp Val Val Ala Gly Lys Pro Leu Asp His Ala Tyr
         35                  40                  45

Val Ser Glu Asn Val Ala Leu Val Glu Ala Gly Cys Val Asn Leu Ala
     50                  55                  60

Lys His Ile Ser Asn Thr Lys Gly Tyr Gly Val Asn Val Val Ala
 65                  70                  75                  80

Ile Asn Lys Phe Ala Thr Asp Thr Asp Ala Glu Met Glu Val Val Lys
                 85                  90                  95

Lys Ala Ala Met Ala Ala Gly Ala
            100
```

<210> SEQ ID NO 25
<211> LENGTH: 479
<212> TYPE: DNA
<213> ORGANISM: Zea mays
<220> FEATURE:
<221> NAME/KEY: unsure
<222> LOCATION: (391)
<220> FEATURE:
<221> NAME/KEY: unsure
<222> LOCATION: (399)
<220> FEATURE:
<221> NAME/KEY: unsure
<222> LOCATION: (429)
<220> FEATURE:
<221> NAME/KEY: unsure
<222> LOCATION: (436)

<400> SEQUENCE: 25

```
aatcaatcaa gacagccccg tgctagctca cccgccgggg ctcgccacga tgagaggcct     60
cctcgcgtgc gccaccctcg cccgccgcgc cgccgcctcc tccgcgcccg cgcgcgtccg    120
ccacctggcg ggcgccgcgg aggcggcgga ggccgagctc aagaggacgg cgctctacga    180
cttccacgtc gcccacggcg gcaagatggt gccgttcgcc ggctggagca tgcccatcca    240
gtacagggac tccatcatgg actccaccgt caactgccgc gccaacggca gcctcttcga    300
cgtcgcccac atgtgcggcc tcagcctcaa gggccgcggg ggccatcccc ttcctcgagt    360
ccctcgtcgt cgccgacgtc gccgcgctca ngggacggna ccgggaacct caccgtcttc    420
accaacgang cagggnnggg gcatcgacga atccgtcatc gccaaggtca ccgaaccaa     479
```

<210> SEQ ID NO 26
<211> LENGTH: 65
<212> TYPE: PRT
<213> ORGANISM: Zea mays

<400> SEQUENCE: 26

| Ala | Ala | Glu | Ala | Glu | Leu | Lys | Arg | Thr | Ala | Leu | Tyr | Asp | Phe | His | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | His | Gly | Gly | Lys | Met | Val | Pro | Phe | Ala | Gly | Trp | Ser | Met | Pro | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Tyr | Arg | Asp | Ser | Ile | Met | Asp | Ser | Thr | Val | Asn | Cys | Arg | Ala | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Ser | Leu | Phe | Asp | Val | Ala | His | Met | Cys | Gly | Leu | Ser | Leu | Lys | Gly |
|-----|-----|-----|-----|-----|-----|-----|-----|-----|-----|-----|-----|-----|-----|-----|-----|
|     | 50  |     |     |     | 55  |     |     |     |     | 60  |     |     |     |     |     |

Arg
65

```
<210> SEQ ID NO 27
<211> LENGTH: 687
<212> TYPE: DNA
<213> ORGANISM: Oryza sativa
<220> FEATURE:
<221> NAME/KEY: unsure
<222> LOCATION: (428)
<220> FEATURE:
<221> NAME/KEY: unsure
<222> LOCATION: (462)
<220> FEATURE:
<221> NAME/KEY: unsure
<222> LOCATION: (496)
<220> FEATURE:
<221> NAME/KEY: unsure
<222> LOCATION: (506)
<220> FEATURE:
<221> NAME/KEY: unsure
<222> LOCATION: (518)
<220> FEATURE:
<221> NAME/KEY: unsure
<222> LOCATION: (521)
<220> FEATURE:
<221> NAME/KEY: unsure
<222> LOCATION: (542)
<220> FEATURE:
<221> NAME/KEY: unsure
<222> LOCATION: (579)
<220> FEATURE:
<221> NAME/KEY: unsure
<222> LOCATION: (585)
<220> FEATURE:
<221> NAME/KEY: unsure
<222> LOCATION: (596)
<220> FEATURE:
<221> NAME/KEY: unsure
<222> LOCATION: (613)
<220> FEATURE:
<221> NAME/KEY: unsure
<222> LOCATION: (622)
<220> FEATURE:
<221> NAME/KEY: unsure
<222> LOCATION: (627)..(628)
<220> FEATURE:
<221> NAME/KEY: unsure
<222> LOCATION: (640)
<220> FEATURE:
<221> NAME/KEY: unsure
<222> LOCATION: (658)..(659)
<220> FEATURE:
<221> NAME/KEY: unsure
<222> LOCATION: (670)
<220> FEATURE:
<221> NAME/KEY: unsure
<222> LOCATION: (683)

<400> SEQUENCE: 27
atcactagaa gatgagaggg ctactcgcgt gcgccacgct cgcccgccgc gccgccggcg   60
cgacgtcgac ggcgcggcgg cacctggcgg gcgcggccga ggcggcggag gcggagctga  120
agaagacggc gctgtacgac ttccacgtcg cgcacggcgg gaagatggtg ccgttcgccg  180
```

```
ggtggagcat gcccatccag tacaaggaca ccatcatgga ctccaccctc aactgccgcg    240
ccaacggcag cctcttcgac gtctcccaca tgtgcgggct cagcctccac gggcgccagg    300
ccatcccctt cctcgagtcc ctcgtcgtcg ccgacgtcgc ggcgctcaag gacggcaacg    360
ggacgctcaa cgtcttcaca acgaccgcgg cgggccatcg acaatccgtc gttacaagtc    420
acgaccanca attactcgtc gtcaacgccg ggtgaaggac angattcgcc acattgggga    480
gcacatggag gcctcnacaa gaaggnggga ctaattgnac ntcacataac gtccttctga    540
tncaggactc ttctgacaat cccatttgca agaagttana aattntcatg ctcaangatg    600
ataatggagc tgnttcccaa anggtanngt aaaagttgan ccgtcacaaa atattttnna    660
ggcccgaaan tagaggaagc gtnggcc                                        687
```

<210> SEQ ID NO 28
<211> LENGTH: 107
<212> TYPE: PRT
<213> ORGANISM: Oryza sativa

<400> SEQUENCE: 28

```
Arg Arg His Leu Ala Gly Ala Ala Glu Ala Ala Glu Ala Glu Leu Lys
  1               5                  10                  15

Lys Thr Ala Leu Tyr Asp Phe His Val Ala His Gly Gly Lys Met Val
             20                  25                  30

Pro Phe Ala Gly Trp Ser Met Pro Ile Gln Tyr Lys Asp Thr Ile Met
         35                  40                  45

Asp Ser Thr Leu Asn Cys Arg Ala Asn Gly Ser Leu Phe Asp Val Ser
     50                  55                  60

His Met Cys Gly Leu Ser Leu His Gly Arg Gln Ala Ile Pro Phe Leu
 65                  70                  75                  80

Glu Ser Leu Val Val Ala Asp Val Ala Ala Leu Lys Asp Gly Asn Gly
                 85                  90                  95

Thr Leu Asn Val Phe Thr Thr Thr Ala Ala Gly
            100                 105
```

<210> SEQ ID NO 29
<211> LENGTH: 571
<212> TYPE: DNA
<213> ORGANISM: Glycine max
<220> FEATURE:
<221> NAME/KEY: unsure
<222> LOCATION: (394)
<220> FEATURE:
<221> NAME/KEY: unsure
<222> LOCATION: (397)
<220> FEATURE:
<221> NAME/KEY: unsure
<222> LOCATION: (425)
<220> FEATURE:
<221> NAME/KEY: unsure
<222> LOCATION: (442)
<220> FEATURE:
<221> NAME/KEY: unsure
<222> LOCATION: (464)
<220> FEATURE:
<221> NAME/KEY: unsure
<222> LOCATION: (484)
<220> FEATURE:
<221> NAME/KEY: unsure
<222> LOCATION: (486)
<220> FEATURE:
<221> NAME/KEY: unsure
<222> LOCATION: (493)
<220> FEATURE:
<221> NAME/KEY: unsure

```
<222> LOCATION: (530)
<220> FEATURE:
<221> NAME/KEY: unsure
<222> LOCATION: (544)
<220> FEATURE:
<221> NAME/KEY: unsure
<222> LOCATION: (553)
<220> FEATURE:
<221> NAME/KEY: unsure
<222> LOCATION: (556)..(557)
<220> FEATURE:
<221> NAME/KEY: unsure
<222> LOCATION: (563)
<220> FEATURE:
<221> NAME/KEY: unsure
<222> LOCATION: (568)..(569)

<400> SEQUENCE: 29
aagccttcct ctctgcagag tgcagagctt tctctccccg ttgcttcatt cattctcaac    60
aacaaaccaa tctttcttag aaaatgaggg ggggcttgtg caacttggg caatcgatca   120 ctcgccgtct tgcccatgga gataagaagg ctgttgctcg tcgatgtttt gcctcagaag   180
ctgagctgaa aaagacagtg tttcatgact ccatgttgc tcatggtggg aagatggttc   240
catttgctgg gtggagcatg ccaatccaat acaaggactc aatcatggac tctaccatca   300
actgtaggga gaatggtagc ctctttgatg tttcccatat gtgtgggctg agcctcaaag   360
ggaaggacgc tgcccccattc cttgaaaagc tggncantgg cgatgttgct gggcttggcc   420
ctggnaatgg gacgttgact gntttcaaaa atgaaaaggg aagngcaatt gatgattcaa   480
ttantnccaa agngaccggt gaccaaatat aattgggtgg gaatgctggn tgcaaggata   540
aagnttgggg canaanntgg ganacatnna g                                  571

<210> SEQ ID NO 30
<211> LENGTH: 142
<212> TYPE: PRT
<213> ORGANISM: Glycine max
<220> FEATURE:
<221> NAME/KEY: UNSURE
<222> LOCATION: (104)..(105)
<220> FEATURE:
<221> NAME/KEY: UNSURE
<222> LOCATION: (120)
<220> FEATURE:
<221> NAME/KEY: UNSURE
<222> LOCATION: (127)
<220> FEATURE:
<221> NAME/KEY: UNSURE
<222> LOCATION: (134)..(135)
<220> FEATURE:
<221> NAME/KEY: UNSURE
<222> LOCATION: (137)

<400> SEQUENCE: 30

Met Arg Gly Gly Leu Trp Gln Leu Gly Gln Ser Ile Thr Arg Arg Leu
  1               5                  10                  15

Ala His Gly Asp Lys Lys Ala Val Ala Arg Arg Cys Phe Ala Ser Glu
             20                  25                  30

Ala Glu Leu Lys Lys Thr Val Phe His Asp Phe His Ala His Gly
         35                  40                  45

Gly Lys Met Val Pro Phe Ala Gly Trp Ser Met Pro Ile Gln Tyr Lys
     50                  55                  60

Asp Ser Ile Met Asp Ser Thr Ile Asn Cys Arg Glu Asn Gly Ser Leu
 65                  70                  75                  80

Phe Asp Val Ser His Met Cys Gly Leu Ser Leu Lys Gly Lys Asp Ala
                 85                  90                  95
```

```
Ala Pro Phe Leu Glu Lys Leu Xaa Xaa Gly Asp Val Ala Gly Leu Gly
        100                 105                 110

Pro Gly Asn Gly Thr Leu Thr Xaa Phe Lys Asn Glu Lys Gly Xaa Ala
    115                 120                 125

Ile Asp Asp Ser Ile Xaa Xaa Lys Xaa Thr Gly Asp Gln Ile
130                 135                 140
```

```
<210> SEQ ID NO 31
<211> LENGTH: 541
<212> TYPE: DNA
<213> ORGANISM: Triticum aestivum
<220> FEATURE:
<221> NAME/KEY: unsure
<222> LOCATION: (260)
<220> FEATURE:
<221> NAME/KEY: unsure
<222> LOCATION: (369)
<220> FEATURE:
<221> NAME/KEY: unsure
<222> LOCATION: (374)
<220> FEATURE:
<221> NAME/KEY: unsure
<222> LOCATION: (447)
<220> FEATURE:
<221> NAME/KEY: unsure
<222> LOCATION: (455)
<220> FEATURE:
<221> NAME/KEY: unsure
<222> LOCATION: (465)
<220> FEATURE:
<221> NAME/KEY: unsure
<222> LOCATION: (468)
<220> FEATURE:
<221> NAME/KEY: unsure
<222> LOCATION: (477)
<220> FEATURE:
<221> NAME/KEY: unsure
<222> LOCATION: (500)
<220> FEATURE:
<221> NAME/KEY: unsure
<222> LOCATION: (507)
<220> FEATURE:
<221> NAME/KEY: unsure
<222> LOCATION: (517)..(518)
<220> FEATURE:
<221> NAME/KEY: unsure
<222> LOCATION: (520)
<220> FEATURE:
<221> NAME/KEY: unsure
<222> LOCATION: (530)

<400> SEQUENCE: 31
gctagctcac ccgccggggc tcgccacgat gagaggcctc ctcgcgtgcg ccaccctcgc    60
ccgccgcgcc gccgcctcct ccgcgcccgc gcgcgtccgc cacctggcgg gcgccgcgga   120
ggcggcggag gccgagctca agaggacggc gctctacgac ttccacgtcg cccacggcgg   180
caagatggtg ccgttcgccg gctggagcat gccatccag tacagggact ccatcatgga   240
ctccaccgtc aactgccgcn ccaacggcag cctcttcgac gtcgcccaca tgtgcgggct   300
cagcctcaag ggccgcgggg ccatcccctt cctcgagtcc ctcgtcgtcg ccgacgtcgc   360
cgcgctcang gacngaaccg gaacctcaac gtcttaacaa cgagcaagga ggcgcatcga   420
cgactccgtc atcgcaaagg taacgtnaca aatcnactcg tcgtnaancc ggatgangga   480
aaggactcgc caatctaggn caatggnggc ttaacannan ggcgggagtn aatggaaatc   540
a                                                                  541
```

```
<210> SEQ ID NO 32
<211> LENGTH: 90
<212> TYPE: PRT
<213> ORGANISM: Triticum aestivum
<220> FEATURE:
<221> NAME/KEY: UNSURE
<222> LOCATION: (47)
<220> FEATURE:
<221> NAME/KEY: UNSURE
<222> LOCATION: (83)
<220> FEATURE:
<221> NAME/KEY: UNSURE
<222> LOCATION: (85)

<400> SEQUENCE: 32
```

Ala Ala Glu Ala Glu Leu Lys Arg Thr Ala Leu Tyr Asp Phe His Val
 1               5                  10                  15

Ala His Gly Gly Lys Met Val Pro Phe Ala Gly Trp Ser Met Pro Ile
            20                  25                  30

Gln Tyr Arg Asp Ser Ile Met Asp Ser Thr Val Asn Cys Arg Xaa Asn
        35                  40                  45

Gly Ser Leu Phe Asp Val Ala His Met Cys Gly Leu Ser Leu Lys Gly
    50                  55                  60

Arg Gly Ala Ile Pro Phe Leu Glu Ser Leu Val Val Ala Asp Val Ala
65                  70                  75                  80

Ala Leu Xaa Asp Xaa Thr Gly Thr Ser Thr
            85                  90

```
<210> SEQ ID NO 33
<211> LENGTH: 536
<212> TYPE: DNA
<213> ORGANISM: Zea mays
<220> FEATURE:
<221> NAME/KEY: unsure
<222> LOCATION: (198)
<220> FEATURE:
<221> NAME/KEY: unsure
<222> LOCATION: (275)
<220> FEATURE:
<221> NAME/KEY: unsure
<222> LOCATION: (307)
<220> FEATURE:
<221> NAME/KEY: unsure
<222> LOCATION: (356)
<220> FEATURE:
<221> NAME/KEY: unsure
<222> LOCATION: (375)
<220> FEATURE:
<221> NAME/KEY: unsure
<222> LOCATION: (420)
<220> FEATURE:
<221> NAME/KEY: unsure
<222> LOCATION: (425)
<220> FEATURE:
<221> NAME/KEY: unsure
<222> LOCATION: (460)
<220> FEATURE:
<221> NAME/KEY: unsure
<222> LOCATION: (516)
<220> FEATURE:
<221> NAME/KEY: unsure
<222> LOCATION: (532)

<400> SEQUENCE: 33
gagcgagtcg aggctccaac cccggcacat cacaggagga ggaggacgac gcgcccacca      60
tggccatggc gacggccctc cgcaagctct ccgccaacgc tctgcgccga cagccgctct     120
cccgcatcac gccgctctac tacatggcgt cccttccggc gacggaggag agatccggaa     180
tcacctggac taagcagntg aacgcgccgc tggaagaggt cgaccccgag attgctgaca     240

```
tcatcgagca cgagaaggcc cgccaatgga agggnctgga gctcatcccg tcggagaatt    300
tcacgtnggt gtcagtgatg cacgcagtgg gttccgtcat gaccaacaag tacagngagg    360
ggtaccctgg cgcangatac tacggcggaa atgagtttat tgatatggca gaagccttgn    420
gtcanaaacc gtgctttgga ggctttccgt ttggacccgn cgaaatgggg agtgaatgtg    480
caacctctat ccggttggcc gccaacttca tggatncctg gactcttgaa gncaca        536
```

```
<210> SEQ ID NO 34
<211> LENGTH: 159
<212> TYPE: PRT
<213> ORGANISM: Zea mays
<220> FEATURE:
<221> NAME/KEY: UNSURE
<222> LOCATION: (47)
<220> FEATURE:
<221> NAME/KEY: UNSURE
<222> LOCATION: (83)
<220> FEATURE:
<221> NAME/KEY: UNSURE
<222> LOCATION: (99)
<220> FEATURE:
<221> NAME/KEY: UNSURE
<222> LOCATION: (106)
<220> FEATURE:
<221> NAME/KEY: UNSURE
<222> LOCATION: (121)..(122)
<220> FEATURE:
<221> NAME/KEY: UNSURE
<222> LOCATION: (134)
<220> FEATURE:
<221> NAME/KEY: UNSURE
<222> LOCATION: (153)
<220> FEATURE:
<221> NAME/KEY: UNSURE
<222> LOCATION: (158)

<400> SEQUENCE: 34
```

Met Ala Met Ala Thr Ala Leu Arg Lys Leu Ser Ala Asn Ala Leu Arg
 1               5                  10                  15

Arg Gln Pro Leu Ser Arg Ile Thr Pro Leu Tyr Tyr Met Ala Ser Leu
            20                  25                  30

Pro Ala Thr Glu Glu Arg Ser Gly Ile Thr Trp Thr Lys Gln Xaa Asn
        35                  40                  45

Ala Pro Leu Glu Glu Val Asp Pro Glu Ile Ala Asp Ile Ile Glu His
    50                  55                  60

Glu Lys Ala Arg Gln Trp Lys Gly Leu Glu Leu Ile Pro Ser Glu Asn
65                  70                  75                  80

Phe Thr Xaa Val Ser Val Met His Ala Val Gly Ser Val Met Thr Asn
                85                  90                  95

Lys Tyr Xaa Glu Gly Tyr Pro Gly Ala Xaa Tyr Tyr Gly Gly Asn Glu
            100                 105                 110

Phe Ile Asp Met Ala Glu Ala Leu Xaa Xaa Lys Pro Cys Phe Gly Gly
        115                 120                 125

Phe Pro Phe Gly Pro Xaa Glu Met Gly Ser Glu Cys Ala Thr Ser Ile
    130                 135                 140

Arg Leu Ala Ala Asn Phe Met Asp Xaa Trp Thr Leu Glu Xaa Thr
145                 150                 155

```
<210> SEQ ID NO 35
<211> LENGTH: 1951
<212> TYPE: DNA
<213> ORGANISM: Oryza sativa

<400> SEQUENCE: 35
```

```
gcacgagtac acaccccgc ctccaccacc acccgccgct cgccgctcgc ccaccatggc      60
catggcgacg cgctccgca agctctcctc cgacgccctc cgccgccagc cgctctcccg     120
catcaccccg ctctactaca tggcgtccct gccggcgacg gaggagagat ccggagtcac    180
ctggccgaag cagctgaacg cgccgctgga ggaggtggat cccgagatcg ccgacatcat    240
cgagcacgag aaggcccgcc aatggaaggg tctggagctc atcccgtcgg agaacttcac    300
ctcggtgtca gtgatgcagg cggtgggatc cgtcatgacc aacaagtaca gcagggggta    360
ccccggcgcg agatactacg gtggaaacga atacattgat atggccgagt cattgtgcca    420
gaaacgtgct ttggaggcct ccgcttgga cccagcgaaa tggggagtga atgtgcaacc     480
tctatcaggg tcacctgcca acttccatgt ttacactgcc ctattgaaac acatgagag    540
aatcatggct ttggatcttc ctcatggtgg acatctttct cacggctacc agactgatac    600
taagaagatt tcagcagttt cgatattctt tgagacaatg ccctacagat tggatgaaag    660
cactggcttg attgattatg atcagatgga gaaagtgcc gttctttta ggccaaagtt     720
gatcgttgcg ggtgcaagtg catatgcgcg tctttatgac tatgaccgca tgcggaaggt    780
ttgtgacaag cagaaggcaa tacttctagc agatatggca catatcagtg gcttgtcgc    840
agctggtgtt gttccatctc cttttgatta tgcagatgta gtgactacca ctactcacaa    900
gtcactccgt ggaccacgtg gagccatgat ctttttacagg aaggggtga aggagtaaa   960
caagcaaggc aaagaggtta tgtatgactt tgaggacaag atcaatgctg ctgtcttccc    1020
aggtctgcaa ggtggaccac ataatcatac cattactggc ttagctgttg cgcttaagca    1080
ggcaactact ccggagtaca gagcttatca agagcaagtt atgagtaact gtgcaaaatt    1140
tgcacagagc ttgacagcaa aaggctacga acttgtctct ggtgggactg acaaccattt    1200
agtgttggta aatctcaaga gcaagggcat agatggttca agagtggaga aggttttaga    1260
aaacgtgcac attgcagcaa acaagaacac agttcctggt gatgtttcag ctatggtacc    1320
aggaggcatc aggatgggaa ccccagcact gacctcaaga ggatttgttg aggaggactt    1380
tgctaaggtt gctgatttct tcgatgcagc agtgaacttg gctttgaagg ttaaggctgc    1440
agcaggtgga acaaaactga aggactttgt tgccactttg caatctgata gcaacattca    1500
atccgagatt gcaaaacttc gccatgatgt ggaggaatat gcaaaacagt tccccacaat    1560
tgggtttgag aaagaaacca tgaagtacaa gaactaagaa actttgaatg gaacagcaag    1620
ggtaaaagaa aaggcatcaa gctgaattcc tgaggtgact gttggaattc ttgcaagaac    1680
aagtcggtgt aaacatatat ccatggagtg ccatcttatg taaagggac ccctggcatt    1740
tacagcgtg tggaaacttt gtcaatagtt cttatcgtag acacctactg taagatgtta    1800
tgctaatgct atattaacct tcactatctt cttggacaag cagttacaca tactttggtg    1860
tattctgtga ataattcgca tgattgcgga attttcgtg tttaaaaaaa aaaaaaaaaa    1920
aaaaaaaaa aaaaaaaaa aaaaaaaaa a                                     1951

<210> SEQ ID NO 36
<211> LENGTH: 513
<212> TYPE: PRT
<213> ORGANISM: Oryza sativa

<400> SEQUENCE: 36

Met Ala Met Ala Thr Ala Leu Arg Lys Leu Ser Ser Asp Ala Leu Arg
 1               5                  10                  15

Arg Gln Pro Leu Ser Arg Ile Thr Pro Leu Tyr Tyr Met Ala Ser Leu
```

```
                    20                  25                  30
Pro Ala Thr Glu Glu Arg Ser Gly Val Thr Trp Pro Lys Gln Leu Asn
            35                  40                  45
Ala Pro Leu Glu Glu Val Asp Pro Glu Ile Ala Asp Ile Ile Glu His
        50                  55                  60
Glu Lys Ala Arg Gln Trp Lys Gly Leu Glu Leu Ile Pro Ser Glu Asn
 65                  70                  75                  80
Phe Thr Ser Val Ser Val Met Gln Ala Val Gly Ser Val Met Thr Asn
                 85                  90                  95
Lys Tyr Ser Glu Gly Tyr Pro Gly Ala Arg Tyr Tyr Gly Gly Asn Glu
                100                 105                 110
Tyr Ile Asp Met Ala Glu Ser Leu Cys Gln Lys Arg Ala Leu Glu Ala
            115                 120                 125
Phe Arg Leu Asp Pro Ala Lys Trp Gly Val Asn Val Gln Pro Leu Ser
        130                 135                 140
Gly Ser Pro Ala Asn Phe His Val Tyr Thr Ala Leu Leu Lys Pro His
145                 150                 155                 160
Glu Arg Ile Met Ala Leu Asp Leu Pro His Gly His Leu Ser His
                165                 170                 175
Gly Tyr Gln Thr Asp Thr Lys Lys Ile Ser Ala Val Ser Ile Phe Phe
            180                 185                 190
Glu Thr Met Pro Tyr Arg Leu Asp Glu Ser Thr Gly Leu Ile Asp Tyr
        195                 200                 205
Asp Gln Met Glu Lys Ser Ala Val Leu Phe Arg Pro Lys Leu Ile Val
    210                 215                 220
Ala Gly Ala Ser Ala Tyr Ala Arg Leu Tyr Asp Tyr Asp Arg Met Arg
225                 230                 235                 240
Lys Val Cys Asp Lys Gln Lys Ala Ile Leu Leu Ala Asp Met Ala His
                245                 250                 255
Ile Ser Gly Leu Val Ala Ala Gly Val Val Pro Ser Pro Phe Asp Tyr
            260                 265                 270
Ala Asp Val Val Thr Thr Thr His Lys Ser Leu Arg Gly Pro Arg
        275                 280                 285
Gly Ala Met Ile Phe Tyr Arg Lys Gly Val Lys Gly Val Asn Lys Gln
290                 295                 300
Gly Lys Glu Val Met Tyr Asp Phe Glu Asp Lys Ile Asn Ala Ala Val
305                 310                 315                 320
Phe Pro Gly Leu Gln Gly Gly Pro His Asn His Thr Ile Thr Gly Leu
                325                 330                 335
Ala Val Ala Leu Lys Gln Ala Thr Thr Pro Glu Tyr Arg Ala Tyr Gln
            340                 345                 350
Glu Gln Val Met Ser Asn Cys Ala Lys Phe Ala Gln Ser Leu Thr Ala
        355                 360                 365
Lys Gly Tyr Glu Leu Val Ser Gly Gly Thr Asp Asn His Leu Val Leu
    370                 375                 380
Val Asn Leu Lys Ser Lys Gly Ile Asp Gly Ser Arg Val Glu Lys Val
385                 390                 395                 400
Leu Glu Asn Val His Ile Ala Ala Asn Lys Asn Thr Val Pro Gly Asp
                405                 410                 415
Val Ser Ala Met Val Pro Gly Gly Ile Arg Met Gly Thr Pro Ala Leu
            420                 425                 430
Thr Ser Arg Gly Phe Val Glu Glu Asp Phe Ala Lys Val Ala Asp Phe
        435                 440                 445
```

```
Phe Asp Ala Ala Val Asn Leu Ala Leu Lys Val Lys Ala Ala Gly
         450                 455                 460

Gly Thr Lys Leu Lys Asp Phe Val Ala Thr Leu Gln Ser Asp Ser Asn
465                 470                 475                 480

Ile Gln Ser Glu Ile Ala Lys Leu Arg His Asp Val Glu Glu Tyr Ala
                485                 490                 495

Lys Gln Phe Pro Thr Ile Gly Phe Glu Lys Glu Thr Met Lys Tyr Lys
            500                 505                 510

Asn

<210> SEQ ID NO 37
<211> LENGTH: 1451
<212> TYPE: DNA
<213> ORGANISM: Glycine max

<400> SEQUENCE: 37
```

| | | | | | |
|---|---|---|---|---|---|
| gcacgagggc | aatggcactt | ggcaggcttt | catcttcctt | caacaagcct | ttacgtcctc | 60 |
| tcttcaatgc | tggctcagtt | tactacaagt | cctctttgcc | tgctgaagct | gcgtacgaca | 120 |
| atgagaaaag | ctgtgatacg | gaattgaatg | ctccacttga | ggttgttgat | cctgagattg | 180 |
| ctgatataat | tgagcttgaa | aaagctagac | aatggaaggg | actggaactg | ataccctccg | 240 |
| agaatttcac | ttctgtctct | gtaatgcaag | ctattggctc | tatcattact | aacactcgga | 300 |
| atgaaggata | tcccggtgca | agatattatg | ggggaaatga | gtatattgac | atggcagaaa | 360 |
| cactatgtca | aaaacgtgcc | ttggaagcat | ttcggttgga | tccggctaaa | tggggagtga | 420 |
| acgtgcagcc | tctgtctggt | tcttctgcca | attttcaagt | ttacactgca | ttgctaaaac | 480 |
| ctcatgatag | aatcatggga | cttgatctac | acatggagg | gcatctttct | catggatacc | 540 |
| agactgacac | caataaggta | tctgcagtct | ccttattttt | tgagacaatg | ccatatagac | 600 |
| tgaacgaaaa | cacgggacac | attgactatg | atcagttgga | gagtacggcg | aaactcttca | 660 |
| ggccaaaatt | aatagttgct | ggagctactg | cttatgcacg | tctgtatgat | tatgcacgca | 720 |
| ttcgcaaggt | gtgtgataaa | cagaaagctg | tgctgttggc | agatatggca | cacatcagtg | 780 |
| gattagttgc | agctggtgtt | atcccttcac | cttttgatta | tgcagatgta | gtgactacca | 840 |
| caactcacaa | atcactccgt | ggccctcgcg | gagctatgat | cttcttcagg | aagggggtaa | 900 |
| aagaaattaa | cgaaaaagga | gaagaggtga | tgtatgacta | tgaagacaaa | atcaatagag | 960 |
| ctgtgtttcc | tggactgcaa | agtggtcctc | acttccactc | tattactggt | ttagctgttg | 1020 |
| cattgaagca | ggctacaact | ccaaactata | gagcatacca | agagcaggtt | ctccgtaatt | 1080 |
| gctcaaaatt | tgcacaggca | ctgagtgaga | agggctatga | gcttgtttct | ggtggaactg | 1140 |
| agaatcatct | acttttggtg | aatctgaaga | gcaagggtat | tgatggctcc | agagttcaga | 1200 |
| aggtgttgga | atcagttcac | attgcagcta | acaaaaacac | agttccagga | gatgtgtccg | 1260 |
| ccatggttcc | tggtggtatc | agaatgggaa | ctcctgctct | tacttctaag | ggatttggct | 1320 |
| aagaagattt | tgttatgggg | gcagagtttt | ttgatgcaac | tgttaattta | gctggtaaga | 1380 |
| ttaagtcaag | gacaaaagga | ttaaaattga | aggacttcct | gggcaaaatt | caatcatcct | 1440 |
| cctaatttca | a | | | | | 1451 |

```
<210> SEQ ID NO 38
<211> LENGTH: 439
<212> TYPE: PRT
<213> ORGANISM: Glycine max
```

-continued

```
<400> SEQUENCE: 38

Thr Arg Ala Met Ala Leu Gly Arg Leu Ser Ser Phe Asn Lys Pro
 1               5                  10                  15

Leu Arg Pro Leu Phe Asn Ala Gly Ser Val Tyr Tyr Lys Ser Ser Leu
            20                  25                  30

Pro Ala Glu Ala Ala Tyr Asp Asn Glu Lys Ser Cys Asp Thr Glu Leu
            35                  40                  45

Asn Ala Pro Leu Glu Val Val Asp Pro Glu Ile Ala Asp Ile Ile Glu
 50                  55                  60

Leu Glu Lys Ala Arg Gln Trp Lys Gly Leu Glu Leu Ile Pro Ser Glu
 65                  70                  75                  80

Asn Phe Thr Ser Val Ser Val Met Gln Ala Ile Gly Ser Ile Ile Thr
                85                  90                  95

Asn Thr Arg Asn Glu Gly Tyr Pro Gly Ala Arg Tyr Tyr Gly Gly Asn
            100                 105                 110

Glu Tyr Ile Asp Met Ala Glu Thr Leu Cys Gln Lys Arg Ala Leu Glu
            115                 120                 125

Ala Phe Arg Leu Asp Pro Ala Lys Trp Gly Val Asn Val Gln Pro Leu
130                 135                 140

Ser Gly Ser Ser Ala Asn Phe Gln Val Tyr Thr Ala Leu Leu Lys Pro
145                 150                 155                 160

His Asp Arg Ile Met Gly Leu Asp Leu Pro His Gly His Leu Ser
                165                 170                 175

His Gly Tyr Gln Thr Asp Thr Asn Lys Val Ser Ala Val Ser Leu Phe
            180                 185                 190

Phe Glu Thr Met Pro Tyr Arg Leu Asn Glu Asn Thr Gly His Ile Asp
            195                 200                 205

Tyr Asp Gln Leu Glu Ser Thr Ala Lys Leu Phe Arg Pro Lys Leu Ile
210                 215                 220

Val Ala Gly Ala Thr Ala Tyr Ala Arg Leu Tyr Asp Tyr Ala Arg Ile
225                 230                 235                 240

Arg Lys Val Cys Asp Lys Gln Lys Ala Val Leu Leu Ala Asp Met Ala
                245                 250                 255

His Ile Ser Gly Leu Val Ala Ala Gly Val Ile Pro Ser Pro Phe Asp
            260                 265                 270

Tyr Ala Asp Val Val Thr Thr Thr His Lys Ser Leu Arg Gly Pro
275                 280                 285

Arg Gly Ala Met Ile Phe Phe Arg Lys Gly Val Lys Glu Ile Asn Glu
290                 295                 300

Lys Gly Glu Glu Val Met Tyr Asp Tyr Glu Asp Lys Ile Asn Arg Ala
305                 310                 315                 320

Val Phe Pro Gly Leu Gln Ser Gly Pro His Phe His Ser Ile Thr Gly
                325                 330                 335

Leu Ala Val Ala Leu Lys Gln Ala Thr Thr Pro Asn Tyr Arg Ala Tyr
            340                 345                 350

Gln Glu Gln Val Leu Arg Asn Cys Ser Lys Phe Ala Gln Ala Leu Ser
            355                 360                 365

Glu Lys Gly Tyr Glu Leu Val Ser Gly Gly Thr Glu Asn His Leu Leu
370                 375                 380

Leu Val Asn Leu Lys Ser Lys Gly Ile Asp Gly Ser Arg Val Gln Lys
385                 390                 395                 400

Val Leu Glu Ser Val His Ile Ala Ala Asn Lys Asn Thr Val Pro Gly
                405                 410                 415
```

Asp Val Ser Ala Met Val Pro Gly Gly Ile Arg Met Gly Thr Pro Ala
            420                 425                 430

Leu Thr Ser Lys Gly Phe Gly
        435

<210> SEQ ID NO 39
<211> LENGTH: 1878
<212> TYPE: DNA
<213> ORGANISM: Triticum aestivum

<400> SEQUENCE: 39

| | | | | | |
|---|---|---|---|---|---|
| ctcgtgccga | attcggcacg | agcctaccga | gaggtgcacg | aggaggccgc | ccaccaccac | 60 |
| cacccaccat | ggccatggcg | acggcgctcc | gcaagctctc | cgcccgcggc | cagcccctct | 120 |
| cccgcctcac | gccgctctac | tccatggcgt | ccctgccggc | gacggaggag | agatccgcag | 180 |
| tcacctggcc | gaagcagttg | aacgcgccgc | tggaggaggt | cgaccccgag | attgccgaca | 240 |
| tcatcgagct | cgagaaggcc | cgccaatgga | agggctgga | gctcatcccg | tcggagaact | 300 |
| tcacctccct | gtcggtgatg | caggcggtgg | gatccgtcat | gaccaacaag | tacagcgagg | 360 |
| ggtaccccgg | cgcgagatac | tacggtggaa | acgaatacat | tgatatggcc | gagacgctgt | 420 |
| gtcagaaacg | tgctttggag | gccttcaatt | tggacccaga | gaagtgggga | gtgaatgtgc | 480 |
| aacctctatc | gggttcacct | gccaacttcc | atgtatacac | tgctctgctg | aagccacatg | 540 |
| acagaattat | ggctctggat | cttcctcacg | gtggacatct | ttcccatggc | taccagactg | 600 |
| acacaaagaa | aatctcagca | gtttcaatat | tctttgagac | aatgccttac | agactggatg | 660 |
| aaagcactgg | cttgattgat | tatgaccagt | tggagaaaag | tgccgttctg | tttaggccaa | 720 |
| agttgattgt | tgctggtgct | agtgcatatg | cccgccttta | tgattataac | cgcatgcgga | 780 |
| agatctgtga | caagcagaag | gcagttcttc | tggcagacat | ggcacatatc | agtgggctag | 840 |
| ttgctgctgg | tgtaattccg | tctccttttg | agtatgcaga | tgtggtgact | accactaccc | 900 |
| acaagtcact | ccgtggtcca | cgtggagcca | tgatcttttt | ccggaaggga | gtgaaagaaa | 960 |
| taaacaaaca | agggaaggag | gttaagtatg | attttgagga | caaaatcaat | gctgctgtct | 1020 |
| tcccaggttt | gcaaggtgga | ccccataacc | atactattac | tggcctggca | gttgcgctta | 1080 |
| agcaggcaac | tactcaggag | tacagagctt | atcaagagca | agttatgagc | aactctgcta | 1140 |
| gatttgctga | gagcttaact | tcaaaaggct | acgatattgt | ttctggtggg | actgataacc | 1200 |
| atttagttt | ggtgaacctc | aagaaaaagg | gaatagatgg | ttcacgtgtg | gagaaggttt | 1260 |
| tagaaaatgt | gcatattgca | gcaaacaaga | acacggttcc | tggtgatgtt | tcagctatgg | 1320 |
| tacccggagg | catcaggatg | ggaaccccg | cacttacatc | aagaggattt | gttgaggagg | 1380 |
| acttcgccaa | ggttgctgac | ttcttcgatt | cggcagtgaa | cttggccttg | aaggttaaag | 1440 |
| ctgcagcagc | aggtaccaaa | ctgaaggact | tgttgccac | tttgcaatcc | gacagcaaca | 1500 |
| tccaagctga | aattgcaaag | cttcgccacg | atgtggagga | atatgcgaaa | caattcccaa | 1560 |
| caattggatt | cgagaaggag | accatgaagt | acaagaacta | agaactgctg | tgtttcaaca | 1620 |
| gcaaaggaag | caaacaagaa | gcacagctga | ggacaagtcc | atgtaaacaa | tagatccatg | 1680 |
| atgaagcgcc | accatatgta | aaggaatcc | aagcatttta | cagaatatgg | gaactttgtc | 1740 |
| gatagtttct | tattgcaggc | acatactgta | agatgcttcg | ctgatatgct | ataaaaaaaa | 1800 |
| aaaaaaaaaa | aaaaaaaaaa | aaaaaaaaaa | aaaaaaaaaa | aaaaaaaaaa | aaaaaaaaaa | 1860 |
| aaaaaaaaaa | aaaaaaaa | | | | | 1878 |

```
<210> SEQ ID NO 40
<211> LENGTH: 510
<212> TYPE: PRT
<213> ORGANISM: Triticum aestivum

<400> SEQUENCE: 40

Met Ala Met Ala Thr Ala Leu Arg Lys Leu Ser Ala Arg Gly Gln Pro
 1               5                  10                  15

Leu Ser Arg Leu Thr Pro Leu Tyr Ser Met Ala Ser Leu Pro Ala Thr
            20                  25                  30

Glu Glu Arg Ser Ala Val Thr Trp Pro Lys Gln Leu Asn Ala Pro Leu
        35                  40                  45

Glu Glu Val Asp Pro Glu Ile Ala Asp Ile Ile Glu Leu Glu Lys Ala
    50                  55                  60

Arg Gln Trp Lys Gly Leu Glu Leu Ile Pro Ser Glu Asn Phe Thr Ser
65                  70                  75                  80

Leu Ser Val Met Gln Ala Val Gly Ser Val Met Thr Asn Lys Tyr Ser
                85                  90                  95

Glu Gly Tyr Pro Gly Ala Arg Tyr Tyr Gly Gly Asn Glu Tyr Ile Asp
            100                 105                 110

Met Ala Glu Thr Leu Cys Gln Lys Arg Ala Leu Glu Ala Phe Asn Leu
        115                 120                 125

Asp Pro Glu Lys Trp Gly Val Asn Val Gln Pro Leu Ser Gly Ser Pro
    130                 135                 140

Ala Asn Phe His Val Tyr Thr Ala Leu Leu Lys Pro His Asp Arg Ile
145                 150                 155                 160

Met Ala Leu Asp Leu Pro His Gly Gly His Leu Ser His Gly Tyr Gln
                165                 170                 175

Thr Asp Thr Lys Lys Ile Ser Ala Val Ser Ile Phe Phe Glu Thr Met
            180                 185                 190

Pro Tyr Arg Leu Asp Glu Ser Thr Gly Leu Ile Asp Tyr Asp Gln Leu
        195                 200                 205

Glu Lys Ser Ala Val Leu Phe Arg Pro Lys Leu Ile Val Ala Gly Ala
    210                 215                 220

Ser Ala Tyr Ala Arg Leu Tyr Asp Tyr Asn Arg Met Arg Lys Ile Cys
225                 230                 235                 240

Asp Lys Gln Lys Ala Val Leu Leu Ala Asp Met Ala His Ile Ser Gly
                245                 250                 255

Leu Val Ala Ala Gly Val Ile Pro Ser Pro Phe Glu Tyr Ala Asp Val
            260                 265                 270

Val Thr Thr Thr Thr His Lys Ser Leu Arg Gly Pro Arg Gly Ala Met
        275                 280                 285

Ile Phe Phe Arg Lys Gly Val Lys Glu Ile Asn Lys Gln Gly Lys Glu
    290                 295                 300

Val Lys Tyr Asp Phe Glu Asp Lys Ile Asn Ala Ala Val Phe Pro Gly
305                 310                 315                 320

Leu Gln Gly Gly Pro His Asn His Thr Ile Thr Gly Leu Ala Val Ala
                325                 330                 335

Leu Lys Gln Ala Thr Thr Gln Glu Tyr Arg Ala Tyr Gln Glu Gln Val
            340                 345                 350

Met Ser Asn Ser Ala Arg Phe Ala Glu Ser Leu Thr Ser Lys Gly Tyr
        355                 360                 365

Asp Ile Val Ser Gly Gly Thr Asp Asn His Leu Val Leu Val Asn Leu
    370                 375                 380
```

```
Lys Lys Lys Gly Ile Asp Gly Ser Arg Val Glu Lys Val Leu Glu Asn
385                 390                 395                 400

Val His Ile Ala Ala Asn Lys Asn Thr Val Pro Gly Asp Val Ser Ala
                405                 410                 415

Met Val Pro Gly Gly Ile Arg Met Gly Thr Pro Ala Leu Thr Ser Arg
                420                 425                 430

Gly Phe Val Glu Glu Asp Phe Ala Lys Val Ala Asp Phe Phe Asp Ser
                435                 440                 445

Ala Val Asn Leu Ala Leu Lys Val Lys Ala Ala Ala Gly Thr Lys
                450                 455                 460

Leu Lys Asp Phe Val Ala Thr Leu Gln Ser Asp Ser Asn Ile Gln Ala
465                 470                 475                 480

Glu Ile Ala Lys Leu Arg His Asp Val Glu Glu Tyr Ala Lys Gln Phe
                485                 490                 495

Pro Thr Ile Gly Phe Glu Lys Glu Thr Met Lys Tyr Lys Asn
                500                 505                 510

<210> SEQ ID NO 41
<211> LENGTH: 660
<212> TYPE: DNA
<213> ORGANISM: Zea mays

<400> SEQUENCE: 41
tgccggttct tcttgccggt tacctgaagc ttatacccac tgaattgatc caggaatacc      60
caaaatccat attaaatatc cacccttctc tccttccggc attcggaggg aaaggtttct    120
atggttcaaa ggtgcataaa gctgttattg cctctggagc aagatactcg ggtccaaccg    180
tacattttgt ggatgagcac tatgataccg gtaaaacgtt agcccagagg gttgtgcctg    240
tgttcgcgga tgacacgcca gagctattgg ctgcaagagt cctccatgag gaacatatgg    300
tctatgttga agcagttgct gctttgtgcg aggaccgcgt cgtatggagg gaagatggtg    360
tcccacttat caaagtcgg acaaatccag ctgtgtacat ctaattgaca atacggcaat    420
agtagcacta ttttggagta ataatggaat ttgtagagcc cttgccactt tcccggtaa    480 aagggtact tagcagttga cgtagggttg atatacaggg cacaacttat ttgccaccga    540
aacatttcca tgcgttggaa gtgagaaaca ttgcccccaa taggccgcag tatccattac    600
tgcatggaac aaggttgaaa ttttaccttg atttgagata actatcaaaa aaaaaaaaaa    660

<210> SEQ ID NO 42
<211> LENGTH: 133
<212> TYPE: PRT
<213> ORGANISM: Zea mays

<400> SEQUENCE: 42

Pro Val Leu Leu Ala Gly Tyr Leu Lys Leu Ile Pro Thr Glu Leu Ile
1               5                   10                  15

Gln Glu Tyr Pro Lys Ser Ile Leu Asn Ile His Pro Ser Leu Leu Pro
                20                  25                  30

Ala Phe Gly Gly Lys Gly Phe Tyr Gly Ser Lys Val His Lys Ala Val
                35                  40                  45

Ile Ala Ser Gly Ala Arg Tyr Ser Gly Pro Thr Val His Phe Val Asp
        50                  55                  60

Glu His Tyr Asp Thr Gly Lys Thr Leu Ala Gln Arg Val Val Pro Val
65                  70                  75                  80

Phe Ala Asp Asp Thr Pro Glu Leu Leu Ala Ala Arg Val Leu His Glu
```

Glu His Met Val Tyr Val Glu Ala Val Ala Ala Leu Cys Glu Asp Arg
          85                  90                  95
                    100                 105                 110

Val Val Trp Arg Glu Asp Gly Val Pro Leu Ile Lys Ser Arg Thr Asn
          115                 120                 125

Pro Ala Val Tyr Ile
          130

<210> SEQ ID NO 43
<211> LENGTH: 471
<212> TYPE: DNA
<213> ORGANISM: Oryza sativa
<220> FEATURE:
<221> NAME/KEY: unsure
<222> LOCATION: (4)
<220> FEATURE:
<221> NAME/KEY: unsure
<222> LOCATION: (71)
<220> FEATURE:
<221> NAME/KEY: unsure
<222> LOCATION: (145)
<220> FEATURE:
<221> NAME/KEY: unsure
<222> LOCATION: (205)
<220> FEATURE:
<221> NAME/KEY: unsure
<222> LOCATION: (259)
<220> FEATURE:
<221> NAME/KEY: unsure
<222> LOCATION: (299)
<220> FEATURE:
<221> NAME/KEY: unsure
<222> LOCATION: (407)
<220> FEATURE:
<221> NAME/KEY: unsure
<222> LOCATION: (459)..(460)
<220> FEATURE:
<221> NAME/KEY: unsure
<222> LOCATION: (471)

<400> SEQUENCE: 43
aaanataacc atgtcaagac gtttccttga gagacatggg atccctatc attacctacc        60 gacaagccca ngaaataaaa gagagcaaga gattttagaa ttggttcaag gtaccgattt      120
tgtggtactg gcaagatata tgcanatatt atctgaaggc tttctcaagg cttatggcaa     180
agatattatt aacatccatc atggncttct tccctcattt aagggaggga atccttcgag     240
acaggccttc aacgctggng taaaattgat cggcgcaacc agccattttg ttaccccana     300
acttgatgct ggcccaatca ttgagcaaat ggttgaacgg gtgtcccaca gagacacgct     360
acagagcttt gtggtgaaat ctgagaacct agagaaacaa tgcctancag aagctataaa     420
gtcgtactgt ggagctccgt gtgctaccaa atgaattgnn gaagacaagt n              471

<210> SEQ ID NO 44
<211> LENGTH: 149
<212> TYPE: PRT
<213> ORGANISM: Oryza sativa
<220> FEATURE:
<221> NAME/KEY: UNSURE
<222> LOCATION: (23)
<220> FEATURE:
<221> NAME/KEY: UNSURE
<222> LOCATION: (47)
<220> FEATURE:
<221> NAME/KEY: UNSURE
<222> LOCATION: (99)
<220> FEATURE:
<221> NAME/KEY: UNSURE
<222> LOCATION: (135)

<400> SEQUENCE: 44

Ile Thr Met Ser Arg Arg Phe Leu Glu Arg His Gly Ile Pro Tyr His
1               5                   10                  15

Tyr Leu Pro Thr Ser Pro Xaa Asn Lys Arg Glu Gln Glu Ile Leu Glu
            20                  25                  30

Leu Val Gln Gly Thr Asp Phe Val Val Leu Ala Arg Tyr Met Xaa Ile
        35                  40                  45

Leu Ser Glu Gly Phe Leu Lys Ala Tyr Gly Lys Asp Ile Ile Asn Ile
    50                  55                  60

His His Gly Leu Leu Pro Ser Phe Lys Gly Gly Asn Pro Ser Arg Gln
65                  70                  75                  80

Ala Phe Asn Ala Gly Val Lys Leu Ile Gly Ala Thr Ser His Phe Val
                85                  90                  95

Thr Pro Xaa Leu Asp Ala Gly Pro Ile Ile Glu Gln Met Val Glu Arg
            100                 105                 110

Val Ser His Arg Asp Thr Leu Gln Ser Phe Val Val Lys Ser Glu Asn
        115                 120                 125

Leu Glu Lys Gln Cys Leu Xaa Glu Ala Ile Lys Ser Tyr Cys Gly Ala
    130                 135                 140

Pro Cys Ala Thr Lys
145

<210> SEQ ID NO 45
<211> LENGTH: 913
<212> TYPE: DNA
<213> ORGANISM: Triticum aestivum

<400> SEQUENCE: 45
gcacgagaga ggctcgcggt gttcgtctca ggcgggggct cgaacttccg gtcgatccac      60
gaggccgttc tgggtgggaa ggtgaacggg gatgttgttg cgctcgtcac cgataagcca     120
ggctgcggtg gcgcggagta tgcaaggtgc aatggcatgc ccgtggtcgt gtttcccaag     180
tcgaaatcgg cgccggaggg ggtctccaca gatgaacttc tgaatgttct gagggatctg     240
aaggtagact ttattctact tgctggttac ttgaagctca tacctggtga gctagttaag     300
tcatttccca gatccatgct gaatatacat ccttcactgc tcccggcatt tggaggcaag     360
ggttattatg gtttgaaagt gcataaagca gttattgcat ctggagccag atactccagga    420
ccaactgtgc acttttgtgga tgagcagttc gacacaggga aaaccttggc ccaaagagtt    480
gtgccagtgt tagccaatga tactccagag caattggctg caaggggttct tcacgaggag    540
caccaagttt acgttgaggc agttgctgcc ttgtgtgagg atcgaattgt gtggcgagac    600
gatggtgtcc cacttatcag aagtcagaca aaccccaatg cgtatacctata attcgtgatc    660
tctgtcctga gatctcctga aaactaatga agtttgtagt gtccgcacca agtgccagtt    720
ttcgccacgg catgtagtca acacacaccg ttggtctgat tgagtgaaat aacatgtcta    780
ataatctggt cccagaaaca taatgtgtac cttgcactgt gttcaactca ttgtatggct    840
tggctttgat gataatgtgt tccggtgtgc ctgaacaaag tttcagtgaa aaaaaaaaa     900
aaaaaaaac tcg                                                         913

<210> SEQ ID NO 46
<211> LENGTH: 216
<212> TYPE: PRT
<213> ORGANISM: Triticum aestivum

<400> SEQUENCE: 46

Ala Arg Glu Arg Leu Ala Val Phe Val Ser Gly Gly Ser Asn Phe
1               5                   10                  15

Arg Ser Ile His Glu Ala Val Leu Gly Gly Lys Val Asn Gly Asp Val
            20                  25                  30

Val Ala Leu Val Thr Asp Lys Pro Gly Cys Gly Gly Ala Glu Tyr Ala
        35                  40                  45

Arg Cys Asn Gly Met Pro Val Val Phe Pro Lys Ser Lys Ser Ala
    50                  55                  60

Pro Glu Gly Val Ser Thr Asp Glu Leu Leu Asn Val Leu Arg Asp Leu

```
                65                  70                  75                  80
Lys Val Asp Phe Ile Leu Leu Ala Gly Tyr Leu Lys Leu Ile Pro Gly
                            85                  90                  95
Glu Leu Val Lys Ser Phe Pro Arg Ser Met Leu Asn Ile His Pro Ser
                100                 105                 110
Leu Leu Pro Ala Phe Gly Gly Lys Gly Tyr Tyr Gly Leu Lys Val His
            115                 120                 125
Lys Ala Val Ile Ala Ser Gly Ala Arg Tyr Ser Gly Pro Thr Val His
        130                 135                 140
Phe Val Asp Glu Gln Phe Asp Thr Gly Lys Thr Leu Ala Gln Arg Val
145                 150                 155                 160
Val Pro Val Leu Ala Asn Asp Thr Pro Glu Gln Leu Ala Ala Arg Val
                165                 170                 175
Leu His Glu Glu His Gln Val Tyr Val Glu Ala Val Ala Ala Leu Cys
                180                 185                 190
Glu Asp Arg Ile Val Trp Arg Asp Asp Gly Val Pro Leu Ile Arg Ser
            195                 200                 205
Gln Thr Asn Pro Asn Ala Tyr Thr
        210                 215

<210> SEQ ID NO 47
<211> LENGTH: 439
<212> TYPE: DNA
<213> ORGANISM: Zea mays

<400> SEQUENCE: 47
gttcagggtt tgggtattc catcgtttcc actggtggaa cagcatccag cctggaagca        60
gcaggagtca gtgtaacaaa agttgaagaa attacacatt tccctgaaat gcttgatgga       120
cgagtgaaaa cattgcaccc aagtatacat ggtggtattc ttgccaggag agaccaggag       180
catcatttga aggcactaaa agatcatgga attgggacat ttgatgtggt tgtggtgaat       240
ttgtatccct tttatgacaa agtcacctct ggtaacatct cttttgagga tggcattgaa       300
aatattgata ttggtgggcc cacgatgatc agagctgcag ccaagaacca taaggatgtt       360
cttattgtgg tggatcataa tgattatcct gctttactgg agtaccttaa aggaaagcga       420
gacgatcagc agttcccca                                                    439

<210> SEQ ID NO 48
<211> LENGTH: 134
<212> TYPE: PRT
<213> ORGANISM: Zea mays

<400> SEQUENCE: 48

Lys Ala Leu Lys Asp His Gly Ile Gly Thr Phe Asp Val Val Val
  1               5                  10                  15
Asn Leu Tyr Pro Phe Tyr Asp Lys Val Thr Ser Gly Asn Ile Ser Phe
                20                  25                  30
Glu Asp Gly Ile Glu Asn Ile Asp Ile Gly Gly Pro Thr Met Ile Arg
            35                  40                  45
Ala Ala Ala Lys Asn His Lys Asp Val Leu Ile Val Leu Gly Tyr Ser
        50                  55                  60
Ile Val Ser Thr Gly Gly Thr Ala Ser Ser Leu Glu Ala Ala Gly Val
 65                 70                  75                  80
Ser Val Thr Lys Val Glu Glu Ile Thr His Phe Pro Glu Met Leu Asp
                85                  90                  95
```

Gly Arg Val Lys Thr Leu His Pro Ser Ile His Gly Gly Ile Leu Ala
            100                 105                 110

Arg Arg Asp Gln Glu His His Leu Val Asp His Asn Asp Tyr Pro Ala
        115                 120                 125

Leu Leu Glu Tyr Leu Lys
    130

<210> SEQ ID NO 49
<211> LENGTH: 1651
<212> TYPE: DNA
<213> ORGANISM: Oryza sativa

<400> SEQUENCE: 49

| | | | | | |
|---|---|---|---|---|---|
| gcacgagctt | acagtgaact | tgtatccatt | ctataacaag | gtcacctctg | gtgtaatttc | 60 |
| tttcgaggat | ggcattgaaa | acattgatat | cggtggacct | acgatgatcc | gagcagcagc | 120 |
| taagaatcat | aaggatgttc | ttgttatggt | ggatcatgaa | gattaccctg | ctctattaga | 180 |
| gtatctgcaa | ggaaaacaag | atgaccagca | attccgcaag | atgctagcat | ggaaagcttt | 240 |
| ccaacatgtc | gcttcttatg | attcagctgt | ctcagaatgg | ttgtggaagc | aatcgaacaa | 300 |
| aggagatgta | ttccccccga | acttcaccgt | gcccctgtcc | ctgaaatcta | cacttcgtta | 360 |
| tggtgaaaat | cctcatcaaa | aagctgcctt | ctatgggac | aagagtcttt | ctgtagttaa | 420 |
| tgctggtggt | attgcaacag | caattcagca | ccatgggaag | gaaatgtctt | acaacaacta | 480 |
| cttagatgcg | gatgctgcat | ggaactgtgt | atcagagttt | gagagtccta | cgtgtgttgt | 540 |
| ggttaagcac | acaaatccat | gtggagtagc | atcccgacag | gatattcttg | aagcatacag | 600 |
| gttggctgta | aagggagatc | ctgttagtgc | atttggtggg | atagttgctt | tcaatacgac | 660 |
| aattgatgag | gtatccagta | gacttcttgc | ctctaaacac | ttgtgttgtt | gggcatgacc | 720 |
| attattcaca | ctatatcatg | tttcaggatc | ttgcaaaaga | aatccgtgaa | ttcaggagcc | 780 |
| ctacagatgg | acagacgcga | atgttctacg | agattgttgt | tgcacccggc | tatacagaaa | 840 |
| agggtcttga | gatcctcaaa | gggaaatcaa | agacattgag | gatactggag | gcgaagagaa | 900 |
| gtggaaaagg | gatgctatca | ctcaggcaag | tcagtggtgg | ctggttggct | caagagtctg | 960 |
| atgatctaac | ccctgaagat | atcaccttca | caacagtgtc | cgagagagct | cctcaagaca | 1020 |
| gtgagctctc | tgatgccaaa | tttgcctggc | tttgtgtaaa | gcacgtaaag | agtaacgcca | 1080 |
| ttgtgatagc | caagaataac | tgcatgttag | gcatgggaag | tggccagcca | aacagactgg | 1140 |
| agagtctgag | aattgctttc | aggaaagcag | gagaggaggc | caaggagct | gctttggcca | 1200 |
| gtgatgcatt | cttcccattc | gcttggaacg | acgccgtgga | ggaggcgtgc | cagaacggca | 1260 |
| tcggcgtgat | cgcggagccg | agcggcagca | tgagggacg | cgacgccgtc | gactgctgca | 1320 |
| acaagtacgg | cgtctccctc | ctcttcaccg | gcgtcaggca | cttcaggcac | tgagctagct | 1380 |
| agcctcatga | accttgatct | tcctgcaaaa | aaggaaaaa | aaacatgggc | atgtcagatc | 1440 |
| gatcgctctt | tctgtatcac | aagagcatgc | agatcgacca | gcgtttgatc | accttgagaa | 1500 |
| aaactcttga | cggcttgtac | taggctgcct | gccactggtg | tgacagaatt | tgatcagctt | 1560 |
| gacattttgc | aataagattc | atggtgataa | taagattagg | atgtctcgta | ctcattctaa | 1620 |
| aaaaaaaaa | aaaaaaaaa | aaaaaaaaa | a | | | 1651 |

<210> SEQ ID NO 50
<211> LENGTH: 456
<212> TYPE: PRT
<213> ORGANISM: Oryza sativa

<400> SEQUENCE: 50

| | | | | | | | | | | | | | | |
|---|---|---|---|---|---|---|---|---|---|---|---|---|---|---|
| His | Glu | Leu | Thr | Val | Asn | Leu | Tyr | Pro | Phe | Tyr | Asn | Lys | Val | Thr | Ser |
| 1 | | | | 5 | | | | | 10 | | | | | 15 | |
| Gly | Val | Ile | Ser | Phe | Glu | Asp | Gly | Ile | Glu | Asn | Ile | Asp | Ile | Gly | Gly |
| | | | 20 | | | | | 25 | | | | | 30 | | |
| Pro | Thr | Met | Ile | Arg | Ala | Ala | Lys | Asn | His | Lys | Asp | Val | Leu | Val |
| | | 35 | | | | | 40 | | | | | 45 | | |
| Met | Val | Asp | His | Glu | Asp | Tyr | Pro | Ala | Leu | Leu | Glu | Tyr | Leu | Gln | Gly |
| | 50 | | | | | 55 | | | | | 60 | | | | |
| Lys | Gln | Asp | Asp | Gln | Gln | Phe | Arg | Lys | Met | Leu | Ala | Trp | Lys | Ala | Phe |
| 65 | | | | | 70 | | | | | 75 | | | | | 80 |
| Gln | His | Val | Ala | Ser | Tyr | Asp | Ser | Ala | Val | Ser | Glu | Trp | Leu | Trp | Lys |
| | | | | 85 | | | | | 90 | | | | | 95 | |
| Gln | Ser | Asn | Lys | Gly | Asp | Val | Phe | Pro | Pro | Asn | Phe | Thr | Val | Pro | Leu |
| | | | 100 | | | | | 105 | | | | | 110 | | |
| Ser | Leu | Lys | Ser | Thr | Leu | Arg | Tyr | Gly | Glu | Asn | Pro | His | Gln | Lys | Ala |
| | | 115 | | | | | 120 | | | | | 125 | | | |
| Ala | Phe | Tyr | Gly | Asp | Lys | Ser | Leu | Ser | Val | Val | Asn | Ala | Gly | Gly | Ile |
| | 130 | | | | | 135 | | | | | 140 | | | | |
| Ala | Thr | Ala | Ile | Gln | His | His | Gly | Lys | Glu | Met | Ser | Tyr | Asn | Asn | Tyr |
| 145 | | | | | 150 | | | | | 155 | | | | | 160 |
| Leu | Asp | Ala | Asp | Ala | Ala | Trp | Asn | Cys | Val | Ser | Glu | Phe | Glu | Ser | Pro |
| | | | | 165 | | | | | 170 | | | | | 175 | |
| Thr | Cys | Val | Val | Val | Lys | His | Thr | Asn | Pro | Cys | Gly | Val | Ala | Ser | Arg |
| | | | 180 | | | | | 185 | | | | | 190 | | |
| Gln | Asp | Ile | Leu | Glu | Ala | Tyr | Arg | Leu | Ala | Val | Lys | Gly | Asp | Pro | Val |
| | | 195 | | | | | 200 | | | | | 205 | | | |
| Ser | Ala | Phe | Gly | Gly | Ile | Val | Ala | Phe | Asn | Thr | Thr | Ile | Asp | Glu | Val |
| | 210 | | | | | 215 | | | | | 220 | | | | |
| Ser | Ser | Arg | Leu | Leu | Pro | Leu | Asn | Thr | Cys | Val | Val | Gly | His | Asp | His |
| 225 | | | | | 230 | | | | | 235 | | | | | 240 |
| Tyr | Ser | His | Tyr | Ile | Met | Phe | Gln | Asp | Leu | Ala | Lys | Glu | Ile | Arg | Glu |
| | | | | 245 | | | | | 250 | | | | | 255 | |
| Phe | Arg | Ser | Pro | Thr | Asp | Gly | Gln | Thr | Arg | Met | Phe | Tyr | Glu | Ile | Val |
| | | | 260 | | | | | 265 | | | | | 270 | | |
| Val | Ala | Pro | Gly | Tyr | Thr | Glu | Lys | Gly | Leu | Glu | Ile | Leu | Lys | Gly | Lys |
| | | 275 | | | | | 280 | | | | | 285 | | | |
| Ser | Lys | Thr | Leu | Arg | Ile | Leu | Glu | Ala | Lys | Arg | Ser | Gly | Lys | Gly | Met |
| | 290 | | | | | 295 | | | | | 300 | | | | |
| Leu | Ser | Leu | Arg | Gln | Val | Ser | Gly | Gly | Trp | Leu | Ala | Gln | Glu | Ser | Asp |
| 305 | | | | | 310 | | | | | 315 | | | | | 320 |
| Asp | Leu | Thr | Pro | Glu | Asp | Ile | Thr | Phe | Thr | Thr | Val | Ser | Glu | Arg | Ala |
| | | | | 325 | | | | | 330 | | | | | 335 | |
| Pro | Gln | Asp | Ser | Glu | Leu | Ser | Asp | Ala | Lys | Phe | Ala | Trp | Leu | Cys | Val |
| | | | 340 | | | | | 345 | | | | | 350 | | |
| Lys | His | Val | Lys | Ser | Asn | Ala | Ile | Val | Ile | Ala | Lys | Asn | Asn | Cys | Met |
| | | 355 | | | | | 360 | | | | | 365 | | | |
| Leu | Gly | Met | Gly | Ser | Gly | Gln | Pro | Asn | Arg | Leu | Glu | Ser | Leu | Arg | Ile |
| | 370 | | | | | 375 | | | | | 380 | | | | |
| Ala | Phe | Arg | Lys | Ala | Gly | Glu | Glu | Ala | Lys | Gly | Ala | Ala | Leu | Ala | Ser |
| 385 | | | | | 390 | | | | | 395 | | | | | 400 |
| Asp | Ala | Phe | Phe | Pro | Phe | Ala | Trp | Asn | Asp | Ala | Val | Glu | Glu | Ala | Cys |
| | | | | 405 | | | | | 410 | | | | | 415 | |

```
Gln Asn Gly Ile Gly Val Ile Ala Glu Pro Ser Gly Met Arg Asp
            420                 425                 430

Gly Asp Ala Val Asp Cys Cys Asn Lys Tyr Gly Val Ser Leu Leu Phe
        435                 440                 445

Thr Gly Val Arg His Phe Arg His
    450                 455

<210> SEQ ID NO 51
<211> LENGTH: 461
<212> TYPE: DNA
<213> ORGANISM: Glycine max

<400> SEQUENCE: 51
ttgggtgttt cttcctccgc cgcagccgct cctgctgctg ccacctcctc cactcaccac      60
cttctcagtg gaacccttca ctctccttct tccctctcaa cttcccatct atttcccaca    120
acttcggtgc gttcatcttc actgcacttc aggtgcgttc caatcaaagc catggctgaa    180
gttgatacta tagcagtgtc aaaaactgct tcttcttctg ctccgggcag caagcaagcc    240
ttgatatcat tgtcagacaa gaaggatctt gcatttgttg ggaatgggct ccaggaatta    300
ggatatacta ttgtttcaac tggaggaaca gcttctgcat ggagagtgc tggagtagct    360 gttactaaag ttgaaaagct cactaagttc cctgaaatgc ttgatggtcg tgtcaaaact    420
ttgcaaccta acatacatgg gggtatcctt gcccgaaggg a                        461

<210> SEQ ID NO 52
<211> LENGTH: 77
<212> TYPE: PRT
<213> ORGANISM: Glycine max

<400> SEQUENCE: 52

Ser Lys Gln Ala Leu Ile Ser Leu Ser Asp Lys Lys Asp Leu Ala Phe
  1               5                  10                  15

Val Gly Asn Gly Leu Gln Glu Leu Gly Tyr Thr Ile Val Ser Thr Gly
             20                  25                  30

Gly Thr Ala Ser Ala Leu Glu Ser Ala Gly Val Ala Val Thr Lys Val
         35                  40                  45

Glu Lys Leu Thr Lys Phe Pro Glu Met Leu Asp Gly Arg Val Lys Thr
     50                  55                  60

Leu Gln Pro Asn Ile His Gly Gly Ile Leu Ala Arg Arg
 65                  70                  75

<210> SEQ ID NO 53
<211> LENGTH: 1206
<212> TYPE: DNA
<213> ORGANISM: Triticum aestivum

<400> SEQUENCE: 53
cttggatgct gatgctgcat ggaattgtgt gtcagagttt gagaatccta cttgtgttgt      60
ggttaagcac accaatccgt gcggtgttgc atcccggcag gatgttcttg aggcatacag    120
gttggccgta aggcagatct ctgtgagtgc atttggcgga atcgttgcat tcaacaccac    180
agttgacgag gatcttgcaa aggagattcg cgagtttaga agtcctacag atggcgagac    240
tcggatgttc tatgagatcg tggtggcacc aggatacaca gagaagggcc tcgaggtcct    300
caaagggaaa tccaagacgt tgaggatcct tgaggcaaag agaagtgggg aaaacatgct    360
gtcgctcagg caggtcagtg gtggttggct agctcaagag tccgacgatc taaccccaga    420
```

-continued

```
agacatcacc ttcacgacgg gttctgagag agctccgacg acagtgagct atcggatgcc    480
aagttcgcct ggctctgcgt gaagcacgtc aagagcaacg ccattgtgat tgccaaggat    540
aattgcatgc tgggcatggg gagcgggcag ccaaacaggg tggacagcct gaggatcgcc    600
ttcaggaaag caggggaggc cgccaaggga gccgctctgg ccagcgacgc cttcttccca    660
ttcccttgga aggatgccgt ggaggaagcg tgtgagaacg catcggcac  gatcgcgcag    720 cctggcggca gcatgaggga caaggatgcc gttgactgct gcaataagta cggcgtgtcc    780
ctcctcttca ccggcgtccg ccacttcagg cactgagcct aacctgagca cttaaggccg    840
tatcaccggt ctatcggtag tcagtccgcc gcggaaactt gcggatgttt gtcgcaataa    900
gacaggcgca ggtgattctg agtccaacta ggattaattg tatgacggtg gcggaagcat    960
tttgccacgt acgcaagtga ggacgcctag gtgttcgtca cattgctgag ccagcagcgg   1020
ctgggtaata acaaggtcgg aaaccaggg  gccatgtact agttaaacca agcaaaaact   1080
gtgtttgtat tcagacgtcg acatgaatcc aacttgtgag gccattctga ccttttcaaa   1140
aaaaaaaaaa aaaaaaaaaa aaaaaaaaaa aaaaaaaaaa aaaaaaaaaa aaaaaaaaaa   1200
aaaaaa                                                              1206
```

<210> SEQ ID NO 54
<211> LENGTH: 284
<212> TYPE: PRT
<213> ORGANISM: Triticum aestivum

<400> SEQUENCE: 54

```
Leu Asp Ala Asp Ala Ala Trp Asn Cys Val Ser Glu Phe Glu Asn Pro
  1               5                  10                  15

Thr Cys Val Val Val Lys His Thr Asn Pro Cys Gly Val Ala Ser Arg
                 20                  25                  30

Gln Asp Val Leu Glu Ala Tyr Arg Leu Ala Val Arg Ala Asp Pro Val
             35                  40                  45

Ser Ala Phe Gly Gly Ile Val Ala Phe Asn Thr Thr Val Asp Glu Asp
         50                  55                  60

Leu Ala Lys Glu Ile Arg Glu Phe Arg Ser Pro Thr Asp Gly Glu Thr
 65                  70                  75                  80

Arg Met Phe Tyr Glu Ile Val Val Ala Pro Gly Tyr Thr Glu Lys Gly
                 85                  90                  95

Leu Glu Val Leu Lys Gly Lys Ser Lys Thr Leu Arg Ile Leu Glu Ala
            100                 105                 110

Lys Arg Ser Gly Glu Asn Met Leu Ser Leu Arg Gln Val Ser Gly Gly
        115                 120                 125

Trp Leu Ala Gln Glu Ser Asp Asp Leu Thr Pro Glu Asp Ile Thr Phe
130                 135                 140

Thr Thr Gly Ser Glu Arg Ala Pro Thr Thr Val Ser Tyr Arg Met Pro
145                 150                 155                 160

Ser Ser Pro Gly Ser Ala Asp Ser Glu Leu Ser Asp Ala Lys Phe Ala
                165                 170                 175

Trp Leu Cys Val Lys His Val Lys Ser Asn Ala Ile Val Ile Ala Lys
            180                 185                 190

Asp Asn Cys Met Leu Gly Met Gly Ser Gly Gln Pro Asn Arg Val Asp
        195                 200                 205

Ser Leu Arg Ile Ala Phe Arg Lys Ala Gly Glu Ala Ala Lys Gly Ala
    210                 215                 220

Ala Leu Ala Ser Asp Ala Phe Phe Pro Phe Pro Trp Lys Asp Ala Val
```

```
                225                 230                 235                 240
Glu Glu Ala Cys Glu Asn Gly Ile Gly Thr Ile Ala Gln Pro Gly Gly
                245                 250                 255

Ser Met Arg Asp Lys Asp Ala Val Asp Cys Cys Asn Lys Tyr Gly Val
            260                 265                 270

Ser Leu Leu Phe Thr Gly Val Arg His Phe Arg His
            275                 280

<210> SEQ ID NO 55
<211> LENGTH: 1097
<212> TYPE: DNA
<213> ORGANISM: Zea mays

<400> SEQUENCE: 55
gatttgctaa cattgctcat ggaaactctt caattgttgc tgataagatt gctttgaagt      60
tggttgggaa gggtggcttt gttgttactg aggcaggttt tggtgctgat attggaactg     120
agaagttcat ggacatcaaa tgtaggtata gtggattggt gccgcagtgt gctattatcg     180
tggccacaat tagagctctt aaaatgcatg agggggggcc tgaagtggtg gctggaaagc     240
ctctggatca tgcatatgtg agcgaaaatg tggcccttgt tgaagctgga tgtattaatc     300
ttgctaaaca tatatcaaac acgaggagtt atggagttaa tgttgtagtt gcaatcaaca     360
aatttgcatc agatactgag gcagaaatga aggcagtgca cagtgcagct atggctgctg     420
gtgcttttga cgctgttgtc tgcacacacc atgcccatgg tggtaaagga gcggttgagc     480
ttggacttgc tgttcaacga gcatgcgaaa gccaggcaga acctctgaag ttttttgtatc     540
ccttggaatc tagcataaag gagaagattg agtcaattgc taagttctat ggtgctagtg     600
gcgttgaata ttccgagcag gctgagaagc agattgagat gtacaccaag caagggttct     660
ccagcctccc catttgcatg gcgaagaccc agtactcatt ctcacatgtc ccgtccatga     720
agggcgcccc gaccggcttt gttctgccga taagagacgt gagggccagc atcggcgctg     780
ggttcatcta cccgctcgtg ggcaccatga gcacgatgcc tggccttccc accagaccct     840
gcttctacca gatcgacgtc gacactgcca ccgggaaggt catgggctg tcatgaattg      900
aagtccctga tggtatcatt cagagaacgt aaattcgggg cattcctgga tcgagttaaa     960
taagagccgt tcctggcatc ctgcaagttc agtgccgctt cctttttactt gattttgtaa    1020
accggagact gtaaatgtgc ttgaaccgtg cttttagacc catgcctgaa atcctgcatc    1080
caataagcgt ctcggca                                                   1097

<210> SEQ ID NO 56
<211> LENGTH: 297
<212> TYPE: PRT
<213> ORGANISM: Zea mays

<400> SEQUENCE: 56

Phe Ala Asn Ile Ala His Gly Asn Ser Ser Ile Val Ala Asp Lys Ile
  1               5                  10                  15

Ala Leu Lys Leu Val Gly Lys Gly Gly Phe Val Val Thr Glu Ala Gly
                 20                  25                  30

Phe Gly Ala Asp Ile Gly Thr Glu Lys Phe Met Asp Ile Lys Cys Arg
             35                  40                  45

Tyr Ser Gly Leu Val Pro Gln Cys Ala Ile Ile Val Ala Thr Ile Arg
         50                  55                  60

Ala Leu Lys Met His Gly Gly Gly Pro Glu Val Val Ala Gly Lys Pro
 65                  70                  75                  80
```

```
Leu Asp His Ala Tyr Val Ser Glu Asn Val Ala Leu Val Glu Ala Gly
                85                  90                  95
Cys Ile Asn Leu Ala Lys His Ile Ser Asn Thr Arg Ser Tyr Gly Val
            100                 105                 110
Asn Val Val Ala Ile Asn Lys Phe Ala Ser Asp Thr Glu Ala Glu
        115                 120                 125
Met Lys Ala Val His Ser Ala Ala Met Ala Ala Gly Ala Phe Asp Ala
    130                 135                 140
Val Val Cys Thr His His Ala His Gly Lys Gly Ala Val Glu Leu
145                 150                 155                 160
Gly Leu Ala Val Gln Arg Ala Cys Glu Ser Gln Ala Glu Pro Leu Lys
                165                 170                 175
Phe Leu Tyr Pro Leu Glu Ser Ser Ile Lys Glu Lys Ile Glu Ser Ile
            180                 185                 190
Ala Lys Phe Tyr Gly Ala Ser Gly Val Glu Tyr Ser Gln Ala Glu
        195                 200                 205
Lys Gln Ile Glu Met Tyr Thr Lys Gln Gly Phe Ser Ser Leu Pro Ile
    210                 215                 220
Cys Met Ala Lys Thr Gln Tyr Ser Phe Ser His Val Pro Ser Met Lys
225                 230                 235                 240
Gly Ala Pro Thr Gly Phe Val Leu Pro Ile Arg Asp Val Arg Ala Ser
                245                 250                 255
Ile Gly Ala Gly Phe Ile Tyr Pro Leu Val Gly Thr Met Ser Thr Met
            260                 265                 270
Pro Gly Leu Pro Thr Arg Pro Cys Phe Tyr Gln Ile Asp Val Asp Thr
        275                 280                 285
Ala Thr Gly Lys Val Met Gly Leu Ser
    290                 295

<210> SEQ ID NO 57
<211> LENGTH: 1027
<212> TYPE: DNA
<213> ORGANISM: Oryza sativa

<400> SEQUENCE: 57
gcacgagctt acaattagag ctcttaaaat gcatggtggg ggccctgatg ttgtggctgg    60
gaagcctttg gatcatgcat atgtgagtga aaatgtggct cttgttgaag ctggatgcgt   120
caatcttgct aaacatatcg caaacacaaa gagttatgga gttaatgttg tagttgcaat   180
caacaagttt gcatcagata ctgaagcaga atggacgtg gtgcgaaatg cgtctttggc   240
tgctggtgct tttgatgctg ttgtctgcac tcaccatgcg catggtggta aaggagcggt   300
tgatcttgga ctcgcggttc aacgggcatg tgagagccag gcagaccctc tgaaattttt   360
gtatccttta gaatctggca taaggagaaa gattgagtca atagctaagt tctatggtgc   420
tagcggcgtt gaatactctg aacaggcgga gaagcagatt gaaatgtata ccaagcaagg   480
cttctcaaac ctcccaatat gcatggcgaa aactcagtac tcgttttcgc atgttccatc   540
catgaagggc gcgccgtctg gcttcgtgct tcctatcagg gatgtgaggg ccagcattgg   600
agccggtttc atctacccac tggttggcac catgagcaca atgcctggtc ttcctacaag   660
gccctgcttc tacgaaatcg acgtcgacac agccactggc aaagtcatgg gtctgtcata   720
agcgtttctg gaatggattg caatttgggg cacaattgtg tagttgcaaa ttttgggaca   780
ttcccttagc tgaataatag cctcagtggc ttcctgcaag tgcagcaata cattttctt    840
```

```
tttgagtttc ttggtgactg taaatcagta aatgtggtcg aaccatactg ttcagactct       900
gttccaatgc cccatgtttc agcttaacat gctttctctg attcttccaa aaaaaaaaa       960 aaaaaaaaaa aaaaaaaaaa aaaaacaaaa aaaaaaaaaa aaaaaaaaaa aaaaaaaaaa      1020
aaaaaaa                                                               1027
```

```
<210> SEQ ID NO 58
<211> LENGTH: 239
<212> TYPE: PRT
<213> ORGANISM: Oryza sativa

<400> SEQUENCE: 58

His Glu Leu Thr Ile Arg Ala Leu Lys Met His Gly Gly Pro Asp
 1               5                  10                  15

Val Val Ala Gly Lys Pro Leu Asp His Ala Tyr Val Ser Glu Asn Val
            20                  25                  30

Ala Leu Val Glu Ala Gly Cys Val Asn Leu Ala Lys His Ile Ala Asn
        35                  40                  45

Thr Lys Ser Tyr Gly Val Asn Val Val Ala Ile Asn Lys Phe Ala
    50                  55                  60

Ser Asp Thr Glu Ala Glu Met Asp Val Val Arg Asn Ala Ser Leu Ala
65                  70                  75                  80

Ala Gly Ala Phe Asp Ala Val Val Cys Thr His His Ala His Gly Gly
                85                  90                  95

Lys Gly Ala Val Asp Leu Gly Leu Ala Val Gln Arg Ala Cys Glu Ser
            100                 105                 110

Gln Ala Asp Pro Leu Lys Phe Leu Tyr Pro Leu Glu Ser Gly Ile Lys
        115                 120                 125

Glu Lys Ile Glu Ser Ile Ala Lys Phe Tyr Gly Ala Ser Gly Val Glu
    130                 135                 140

Tyr Ser Glu Gln Ala Glu Lys Gln Ile Glu Met Tyr Thr Lys Gln Gly
145                 150                 155                 160

Phe Ser Asn Leu Pro Ile Cys Met Ala Lys Thr Gln Tyr Ser Phe Ser
                165                 170                 175

His Val Pro Ser Met Lys Gly Ala Pro Ser Gly Phe Val Leu Pro Ile
            180                 185                 190

Arg Asp Val Arg Ala Ser Ile Gly Ala Gly Phe Ile Tyr Pro Leu Val
        195                 200                 205

Gly Thr Met Ser Thr Met Pro Gly Leu Pro Thr Arg Pro Cys Phe Tyr
    210                 215                 220

Glu Ile Asp Val Asp Thr Ala Thr Gly Lys Val Met Gly Leu Ser
225                 230                 235

<210> SEQ ID NO 59
<211> LENGTH: 2202
<212> TYPE: DNA
<213> ORGANISM: Glycine max

<400> SEQUENCE: 59
gcacgagctg aaatcttagt ttctgcccga aactgaaact gaatcgaaat tcaatacaat        60
gagttcctca actacagtga ggaagttgca ggtggtgtcc cctgttcctg cggacataga       120
cattgcaaac tccgttgaac ccgttcatat ctcccagatt gccaaagacc tcaaccttag       180
tcccaatcac tatgaccttt acggtaaata caaggctaag gttttgttgt cggttcttga       240
tgagcttcaa ggatcagaag atgggtatta tgttgtggtc ggaggcatta ctccgactcc       300
```

```
tctcggggaa ggcaaatcta ctactacagt ggggctctgt caagctttag gtgcttttct      360
tgataaaaag gtagtcacct gccttcgtca accatcgcaa ggacctactt ttggaattaa      420
aggaggtgca gctggtggtg gctatagcca agttattccc atggatgaat tcaatcttca      480
tctaacagga gatattcatg caataactgc agcaaacaat cttctagctg ctgcaattga      540
tacccgaatt ttccatgagt caacacagtc agataaggcc ttttttaacc ggttgtgccc      600
tccaaataaa gaagggaaaa ggagctttag tgatgtcatg ttcaggcgtc ttacgaagct      660
tggcatttca aagaccaatc cagatgatct tacaccagaa gaagtaaata aatttgctag      720
gcttgatatt gacccaaatt ctatcacatg gaggagagta atggacatca atgatcgatt      780
cttgagaaaa attgctattg ccagggacc tgacgagaaa ggaatggtga gagaaacagg      840
ctttgatatt tcagttgcta gtgagattat ggctgttttg gcactgacaa catccttagc      900
tgatatgcga gagaggcttg ggaaaatggt tattgggaat agcaagagtg gtgaccctgt      960
aactgctgat gatctaggtg ttggaggtgc tttaacagtt ttaatgaagg atgccattca     1020 ccctacccctt atgcagactc tggaaggaac tcctgttctt gttcatgcag gtccatttgc     1080
aaatattgct catgggaatt cttctattgt ggctgataag attgcactaa agttagttgg     1140
accaggtgga tttgtagtta ctgaagctgg ttttggtgct gatattggag ctgaaaagtt     1200
tatgaacatt aagtgtcgtt atagtggttt gacacctcaa tgtgcgatta ttgtggcaac     1260
tatcagagca ctaaaaatgc atggtggagg gcctgcagtt gttgctggaa gacctcttga     1320
ccatgcatat ttgactgaaa atgttgccct ggttgaggcc ggtgtgtga acatggcacg     1380 acatatatca aatacaaaat cttatggtgt aaatgttgta gttgccatca acaagttttc     1440
aactgacact gaagccgagc taaatgcagt tcgaagtgct gcattagctg ctggagctta     1500
tgatgctgta atttgtaccc atcatgcgaa tggtggcaaa ggagccgttg acctgggcat     1560
tgcagttcaa aaagcctgcg agaatgtgac acagccattg aagttcctgt atcctgttga     1620
cctgagtata aaagagaaaa tagaggcaat agcaaagtca tatggagcca gtggtgttga     1680
gtactcagaa caggctgaga agcagattga gatgtatagc aagcaaggat ttcaggtct      1740 tccaatatgc atggctaaga ctcagtattc tttctcagac aatgctgcag caaagggagc     1800
tccaagtggg tttgtcttac ccataaggga tgtaagagct agtataggcg ctggattat      1860 ttatccttta gttggaacaa tgagtacgat gccagggctt cctacaaggc catgcttcta     1920
tgacattgat ctggatacaa caactggaaa agtcattggt ctctcttaaa tcaaagtgac     1980
ttgttctatc acctttcaaa agctttatgg atgtcattta catatctccc tttgcgatgt     2040
tcatgaacct cacagtaaca ttcctccttg tttgtttgcg tgcttggtga tctgtatgaa     2100
tgaaataaat acgtgattta aggaaaaaaa aaaaaaaaa aaaaaaaaaa aaaaaaaaa      2160 aaaaaaaaa aaaaaaaa aaaaaaaa aaaaaaaaa aa                             2202
```

<210> SEQ ID NO 60
<211> LENGTH: 636
<212> TYPE: PRT
<213> ORGANISM: Glycine max

<400> SEQUENCE: 60

```
Met Ser Ser Ser Thr Thr Val Arg Lys Leu Gln Val Val Ser Pro Val
 1               5                  10                  15

Pro Ala Asp Ile Asp Ile Ala Asn Ser Val Glu Pro Val His Ile Ser
            20                  25                  30

Gln Ile Ala Lys Asp Leu Asn Leu Ser Pro Asn His Tyr Asp Leu Tyr
```

-continued

```
                 35                  40                  45
Gly Lys Tyr Lys Ala Lys Val Leu Leu Ser Val Leu Asp Glu Leu Gln
             50                  55                  60
Gly Ser Glu Asp Gly Tyr Tyr Val Val Gly Ile Thr Pro Thr
 65                  70                  75                  80
Pro Leu Gly Glu Gly Lys Ser Thr Thr Thr Val Gly Leu Cys Gln Ala
                 85                  90                  95
Leu Gly Ala Phe Leu Asp Lys Lys Val Val Thr Cys Leu Arg Gln Pro
                100                 105                 110
Ser Gln Gly Pro Thr Phe Gly Ile Lys Gly Ala Ala Gly Gly Gly
             115                 120                 125
Tyr Ser Gln Val Ile Pro Met Asp Glu Phe Asn Leu His Leu Thr Gly
            130                 135                 140
Asp Ile His Ala Ile Thr Ala Ala Asn Asn Leu Leu Ala Ala Ala Ile
145                 150                 155                 160
Asp Thr Arg Ile Phe His Glu Ser Thr Gln Ser Asp Lys Ala Leu Phe
                165                 170                 175
Asn Arg Leu Cys Pro Pro Asn Lys Glu Gly Lys Arg Ser Phe Ser Asp
                180                 185                 190
Val Met Phe Arg Arg Leu Thr Lys Leu Gly Ile Ser Lys Thr Asn Pro
            195                 200                 205
Asp Asp Leu Thr Pro Glu Glu Val Asn Lys Phe Ala Arg Leu Asp Ile
            210                 215                 220
Asp Pro Asn Ser Ile Thr Trp Arg Arg Val Met Asp Ile Asn Asp Arg
225                 230                 235                 240
Phe Leu Arg Lys Ile Ala Ile Gly Gln Gly Pro Asp Glu Lys Gly Met
                245                 250                 255
Val Arg Glu Thr Gly Phe Asp Ile Ser Val Ala Ser Glu Ile Met Ala
            260                 265                 270
Val Leu Ala Leu Thr Thr Ser Leu Ala Asp Met Arg Glu Arg Leu Gly
            275                 280                 285
Lys Met Val Ile Gly Asn Ser Lys Ser Gly Asp Pro Val Thr Ala Asp
            290                 295                 300
Asp Leu Gly Val Gly Gly Ala Leu Thr Val Leu Met Lys Asp Ala Ile
305                 310                 315                 320
His Pro Thr Leu Met Gln Thr Leu Glu Gly Thr Pro Val Leu His
                325                 330                 335
Ala Gly Pro Phe Ala Asn Ile Ala His Gly Asn Ser Ser Ile Val Ala
            340                 345                 350
Asp Lys Ile Ala Leu Lys Leu Val Gly Pro Gly Phe Val Val Thr
            355                 360                 365
Glu Ala Gly Phe Gly Ala Asp Ile Gly Ala Glu Lys Phe Met Asn Ile
            370                 375                 380
Lys Cys Arg Tyr Ser Gly Leu Thr Pro Gln Cys Ala Ile Ile Val Ala
385                 390                 395                 400
Thr Ile Arg Ala Leu Lys Met His Gly Gly Pro Ala Val Val Ala
                405                 410                 415
Gly Arg Pro Leu Asp His Ala Tyr Leu Thr Glu Asn Val Ala Leu Val
                420                 425                 430
Glu Ala Gly Cys Val Asn Met Ala Arg His Ile Ser Asn Thr Lys Ser
            435                 440                 445
Tyr Gly Val Asn Val Val Ala Ile Asn Lys Phe Ser Thr Asp Thr
450                 455                 460
```

-continued

Glu Ala Glu Leu Asn Ala Val Arg Ser Ala Ala Leu Ala Ala Gly Ala
465                 470                 475                 480

Tyr Asp Ala Val Ile Cys Thr His His Ala Asn Gly Gly Lys Gly Ala
                485                 490                 495

Val Asp Leu Gly Ile Ala Val Gln Lys Ala Cys Glu Asn Val Thr Gln
            500                 505                 510

Pro Leu Lys Phe Leu Tyr Pro Val Asp Leu Ser Ile Lys Glu Lys Ile
        515                 520                 525

Glu Ala Ile Ala Lys Ser Tyr Gly Ala Ser Gly Val Glu Tyr Ser Glu
    530                 535                 540

Gln Ala Glu Lys Gln Ile Glu Met Tyr Ser Lys Gln Gly Phe Ser Gly
545                 550                 555                 560

Leu Pro Ile Cys Met Ala Lys Thr Gln Tyr Ser Phe Ser Asp Asn Ala
                565                 570                 575

Ala Ala Lys Gly Ala Pro Ser Gly Phe Val Leu Pro Ile Arg Asp Val
            580                 585                 590

Arg Ala Ser Ile Gly Ala Gly Phe Ile Tyr Pro Leu Val Gly Thr Met
        595                 600                 605

Ser Thr Met Pro Gly Leu Pro Thr Arg Pro Cys Phe Tyr Asp Ile Asp
    610                 615                 620

Leu Asp Thr Thr Thr Gly Lys Val Ile Gly Leu Ser
625                 630                 635

<210> SEQ ID NO 61
<211> LENGTH: 1021
<212> TYPE: DNA
<213> ORGANISM: Triticum aestivum

<400> SEQUENCE: 61
gcacgagggg actgagaaat tcatggacat aaagtgtagg tatagtggat tgacacctca      60
gtgtgctatt attgtggcca caattagggc tcttaaaatg catggaggag cccagatgt      120
tgtggctggg aagcctttag atcatgcata tgtcagtgaa aatgtggctc ttgttgaagc      180
tggatgtgtt aatcttgcta agcacatctc aaacacaaag ggttatggag tgaatgttgt      240
agtagcaatc aacaaatttg caacagacac agacgctgaa atggaagttg tgaaaaaggc      300
ggctatggca gctggggctt cgatgctgt cgtctgctcc caccatgcac acggtggtaa      360
aggagcggtt gatcttggag tcgctgttca aagagcatgt gaaagccagg cagagccct       420
gaagttttta tatcctttag attctagcat aaaagagaag attgagtcaa tagctaagtt      480
ctatggtgct agtggtgttg aatactctga acaggccgaa aagcaaattg agatgtacac      540
caagcaaggc ttctccaacc tcccgatatg catggcgaag actcagtact cctttctca       600
tgttccatcc atgaagggcg cgccgtcagg cttcgtgctg ccgataagag acgtgcgggc      660
cagcatcgga gccggtttca tctacccgct cgtcgggacc atgagcacaa tgcctggtct      720
ccctacaagg ccctgcttct atgaaatcga catcgacacg ccaccggca aagtcatggg      780
tctgtcatga gcttcgctgg caccgtttc taggctggtg gtcctgtgct gttgcgcaat      840
tgaatcgaca gtgtgcagtt tcaattttgg ggacatttcc tgaagcagaa taaacgaata      900
atggccgcat cgggtggctt ggtgcgattg tgggggtag tacatttcag ttacctgatg      960
gatgtagatt tggtcgaacc atagcgtctg tctgtactct gttggtgttc cttatgtttt    1020
g                                                                    1021

-continued

```
<210> SEQ ID NO 62
<211> LENGTH: 262
<212> TYPE: PRT
<213> ORGANISM: Triticum aestivum

<400> SEQUENCE: 62
```

His Glu Gly Thr Glu Lys Phe Met Asp Ile Lys Cys Arg Tyr Ser Gly
 1               5                  10                  15

Leu Thr Pro Gln Cys Ala Ile Ile Val Ala Thr Ile Arg Ala Leu Lys
            20                  25                  30

Met His Gly Gly Gly Pro Asp Val Val Ala Gly Lys Pro Leu Asp His
        35                  40                  45

Ala Tyr Val Ser Glu Asn Val Ala Leu Val Glu Ala Gly Cys Val Asn
    50                  55                  60

Leu Ala Lys His Ile Ser Asn Thr Lys Gly Tyr Gly Val Asn Val Val
65                  70                  75                  80

Val Ala Ile Asn Lys Phe Ala Thr Asp Thr Asp Ala Glu Met Glu Val
                85                  90                  95

Val Lys Lys Ala Ala Met Ala Ala Gly Ala Phe Asp Ala Val Val Cys
            100                 105                 110

Ser His His Ala His Gly Gly Lys Gly Ala Val Asp Leu Gly Val Ala
        115                 120                 125

Val Gln Arg Ala Cys Glu Ser Gln Ala Glu Pro Leu Lys Phe Leu Tyr
    130                 135                 140

Pro Leu Asp Ser Ser Ile Lys Glu Lys Ile Glu Ser Ile Ala Lys Phe
145                 150                 155                 160

Tyr Gly Ala Ser Gly Val Glu Tyr Ser Glu Gln Ala Glu Lys Gln Ile
                165                 170                 175

Glu Met Tyr Thr Lys Gln Gly Phe Ser Asn Leu Pro Ile Cys Met Ala
            180                 185                 190

Lys Thr Gln Tyr Ser Phe Ser His Val Pro Ser Met Lys Gly Ala Pro
        195                 200                 205

Ser Gly Phe Val Leu Pro Ile Arg Asp Val Arg Ala Ser Ile Gly Ala
    210                 215                 220

Gly Phe Ile Tyr Pro Leu Val Gly Thr Met Ser Thr Met Pro Gly Leu
225                 230                 235                 240

Pro Thr Arg Pro Cys Phe Tyr Glu Ile Asp Ile Asp Thr Ala Thr Gly
                245                 250                 255

Lys Val Met Gly Leu Ser
            260

```
<210> SEQ ID NO 63
<211> LENGTH: 536
<212> TYPE: DNA
<213> ORGANISM: Zea mays
<220> FEATURE:
<221> NAME/KEY: unsure
<222> LOCATION: (329)
<220> FEATURE:
<221> NAME/KEY: unsure
<222> LOCATION: (378)
<220> FEATURE:
<221> NAME/KEY: unsure
<222> LOCATION: (390)
<220> FEATURE:
<221> NAME/KEY: unsure
<222> LOCATION: (406)
<220> FEATURE:
<221> NAME/KEY: unsure
<222> LOCATION: (410)
<220> FEATURE:
```

```
<221> NAME/KEY: unsure
<222> LOCATION: (419)
<220> FEATURE:
<221> NAME/KEY: unsure
<222> LOCATION: (425)
<220> FEATURE:
<221> NAME/KEY: unsure
<222> LOCATION: (442)
<220> FEATURE:
<221> NAME/KEY: unsure
<222> LOCATION: (457)
<220> FEATURE:
<221> NAME/KEY: unsure
<222> LOCATION: (465)
<220> FEATURE:
<221> NAME/KEY: unsure
<222> LOCATION: (470)
<220> FEATURE:
<221> NAME/KEY: unsure
<222> LOCATION: (477)
<220> FEATURE:
<221> NAME/KEY: unsure
<222> LOCATION: (479)
<220> FEATURE:
<221> NAME/KEY: unsure
<222> LOCATION: (485)
<220> FEATURE:
<221> NAME/KEY: unsure
<222> LOCATION: (494)
<220> FEATURE:
<221> NAME/KEY: unsure
<222> LOCATION: (508)
<220> FEATURE:
<221> NAME/KEY: unsure
<222> LOCATION: (520)
<220> FEATURE:
<221> NAME/KEY: unsure
<222> LOCATION: (525)
<220> FEATURE:
<221> NAME/KEY: unsure
<222> LOCATION: (531)

<400> SEQUENCE: 63
catctaatca atcaagacag ccccgtgcta gctcacccgc cggggctcgc cacgatgaga      60
ggcctcctcg cgtgcgccac cctcgcccgc cgcgccgccg cctcctccgc gcccgcgcgc     120
gtccgccacc tggcgggcgc cgcggaggcg gcggaggccg agctcaagag gacggcgctc     180
tacgacttcc acgtcgccca cggcggcaag atggtgccgt cgccggctg gagcatgccc      240
atccagtaca gggactccat catggactcc accgtcaact gccgcgccaa cggcagcctc     300
ttcgacgtcg cccacatgtg cggcctcang cctcaagggc cgcggggcca ttcccttcct     360
cgagtccctc cgtcgtcncc cgaacggtcn ccgcggctca agggancggn aacggtacnc     420
ttcanctgtc cttcaacaaa cnagcagggg ctgggcncca tccgncgaan tcctctnant     480
cggcncaaag gtcnactgat caaccaanaa tctacctctn gtctnttaaa ngcctg         536
```

<210> SEQ ID NO 64
<211> LENGTH: 105
<212> TYPE: PRT
<213> ORGANISM: Zea mays
<220> FEATURE:
<221> NAME/KEY: UNSURE
<222> LOCATION: (92)

<400> SEQUENCE: 64

Met Arg Gly Leu Leu Ala Cys Ala Thr Leu Ala Arg Arg Ala Ala Ala
 1               5                  10                  15

Ser Ser Ala Pro Ala Arg Val Arg His Leu Ala Gly Ala Ala Glu Ala
            20                  25                  30

```
Ala Glu Ala Glu Leu Lys Arg Thr Ala Leu Tyr Asp Phe His Val Ala
        35                  40                  45

His Gly Gly Lys Met Val Pro Phe Ala Gly Trp Ser Met Pro Ile Gln
 50                  55                  60

Tyr Arg Asp Ser Ile Met Asp Ser Thr Val Asn Cys Arg Ala Asn Gly
 65                  70                  75                  80

Ser Leu Phe Asp Val Ala His Met Cys Gly Leu Xaa Leu Lys Gly Arg
                85                  90                  95

Gly Ala Ile Pro Phe Leu Glu Ser Leu
            100                 105

<210> SEQ ID NO 65
<211> LENGTH: 500
<212> TYPE: DNA
<213> ORGANISM: Oryza sativa
<220> FEATURE:
<221> NAME/KEY: unsure
<222> LOCATION: (286)
<220> FEATURE:
<221> NAME/KEY: unsure
<222> LOCATION: (305)
<220> FEATURE:
<221> NAME/KEY: unsure
<222> LOCATION: (311)
<220> FEATURE:
<221> NAME/KEY: unsure
<222> LOCATION: (384)
<220> FEATURE:
<221> NAME/KEY: unsure
<222> LOCATION: (409)
<220> FEATURE:
<221> NAME/KEY: unsure
<222> LOCATION: (411)
<220> FEATURE:
<221> NAME/KEY: unsure
<222> LOCATION: (418)
<220> FEATURE:
<221> NAME/KEY: unsure
<222> LOCATION: (436)
<220> FEATURE:
<221> NAME/KEY: unsure
<222> LOCATION: (455)
<220> FEATURE:
<221> NAME/KEY: unsure
<222> LOCATION: (464)
<220> FEATURE:
<221> NAME/KEY: unsure
<222> LOCATION: (472)
<220> FEATURE:
<221> NAME/KEY: unsure
<222> LOCATION: (489)
<220> FEATURE:
<221> NAME/KEY: unsure
<222> LOCATION: (494)

<400> SEQUENCE: 65
gtttaaaccg gtggtgaaag aagatgagag ggctactcgc gtgcgccacg ctcgcccgcc      60
gcgccgccgg cgcgacgtcg acggcgcggc ggcacctggc gggcgcggcc gaggcggcgg     120
aggcggagct gaagaagacg gcgctgtacg acttccacgt cgcgcacggc gggaagatgg     180
tgccgttcgc cgggtggagc atgcccatcc agtacaagga caccatcatg gactccaccc     240
tcaactgccg cgccaacggc agcctcttcg acgtctccca catgtncggc ctcagcctcc     300
acggncgcca ngccatcccc ttcctcgatc cctcgtcgtc gcgactctcg gcgctcaaag     360
gacggaacgg gagctcacct tttnaacaaa cgaccgctgc ggggcatcna natccgtntt     420
acaaggcacc ggacancaat cactccgtgt caacncgggt gcangacatg tntccccaca     480
ttgggagana tggngctcaa                                                 500
```

<210> SEQ ID NO 66
<211> LENGTH: 159
<212> TYPE: PRT
<213> ORGANISM: Oryza sativa
<220> FEATURE:
<221> NAME/KEY: UNSURE
<222> LOCATION: (88)
<220> FEATURE:
<221> NAME/KEY: UNSURE
<222> LOCATION: (96)
<220> FEATURE:
<221> NAME/KEY: UNSURE
<222> LOCATION: (121)
<220> FEATURE:
<221> NAME/KEY: UNSURE
<222> LOCATION: (129)..(130)
<220> FEATURE:
<221> NAME/KEY: UNSURE
<222> LOCATION: (132)
<220> FEATURE:
<221> NAME/KEY: UNSURE
<222> LOCATION: (138)
<220> FEATURE:
<221> NAME/KEY: UNSURE
<222> LOCATION: (147)
<220> FEATURE:
<221> NAME/KEY: UNSURE
<222> LOCATION: (150)
<220> FEATURE:
<221> NAME/KEY: UNSURE
<222> LOCATION: (156)

<400> SEQUENCE: 66

```
Met Arg Gly Leu Leu Ala Cys Ala Thr Leu Ala Arg Arg Ala Ala Gly
  1               5                  10                  15

Ala Thr Ser Thr Ala Arg Arg His Leu Ala Gly Ala Ala Glu Ala Ala
             20                  25                  30

Glu Ala Glu Leu Lys Lys Thr Ala Leu Tyr Asp Phe His Val Ala His
         35                  40                  45

Gly Gly Lys Met Val Pro Phe Ala Gly Trp Ser Met Pro Ile Gln Tyr
     50                  55                  60

Lys Asp Thr Ile Met Asp Ser Thr Leu Asn Cys Arg Ala Asn Gly Ser
 65                  70                  75                  80

Leu Phe Asp Val Ser His Met Xaa Gly Leu Ser Leu His Gly Arg Xaa
                 85                  90                  95

Ala Ile Pro Phe Leu Asp Pro Ser Ser Arg Leu Ser Ala Leu Lys
            100                 105                 110

Gly Arg Asn Gly Ser Ser Pro Phe Xaa Gln Thr Thr Ala Ala Gly His
        115                 120                 125

Xaa Xaa Pro Xaa Tyr Lys Ala Pro Asp Xaa Asn His Ser Val Ser Thr
130                 135                 140

Arg Val Xaa Asp Met Xaa Pro His Ile Gly Arg Xaa Gly Ala Gln
145                 150                 155
```

<210> SEQ ID NO 67
<211> LENGTH: 1431
<212> TYPE: DNA
<213> ORGANISM: Glycine max

<400> SEQUENCE: 67

```
gcacgagaag ccttcctctc tgcagagtgc agagctttct ctccccgttg cttcattcat      60
tctcaacaac aaaccaatct ttcttagaaa atgaggggg gcttgtggca acttgggcaa     120
tcgatcactc gccgtcttgc ccatggagat aagaaggctg ttgctcgtcg atgttttgcc    180
```

```
tcagaagctg agctgaaaaa gacagtgttt catgacttcc atgttgctca tggtgggaag    240
atggttccat tgctgggtg gagcatgcca atccaataca aggactcaat catggactct    300
accatcaact gtagggagaa tggtagcctc tttgatgttt cccatatgtg tgggctgagc    360
ctcaaaggga aggacgctgc cccattcctt gaaaagctgg tcattgccga tgttgctggg    420
cttgcccctg gaactgggac gttgactgtt ttcacaaatg aaaagggagg tgcaattgat    480
gattcagtaa ttactaaggt gacggatgac cacatatatt tggttgtgaa tgctggctgc    540
agggataaag atctggctca tattgaggaa cacatgaaag cattcaaggc caaaggtggt    600
gatgtgtctt ggcacatcca cgatgagaga tccctacttg ctctgcaggg tcctcttgct    660
gcccccgttc ttcaacacct gacaaaagag gatttgagca agctctactt ggggagttc    720 cgtgtgttgg acatcaatgg ctcagagtgt tttcttacca ggacagggta tactggggaa    780
gatggatttg agatctcagt tccttcagag catggagtag atcttgccaa gcaatactg    840 gaaaaatctg aagggaaggt aagattgaca ggattgggag ctagagatag tctgcgactt    900
gaagctggat tgtgcttata tggaaatgac atggaacagc acattacacc tattgaggca    960
ggactaacat gggctatagg gaagaggagg agagcagaag gtggttttct aggagctgat   1020
gttatcctga aacagcttga agaaggtcct aaaatcaggc gtgttggttt cttttcttct   1080
ggtccacctc ccagaagcca cagtgagatt caagatgaag gaggcaacaa cattgggaa    1140 atcaccagtg gtggattcag tccttgcctc cagaagaaca tagccatggg atatgtgaaa   1200
tctggattgc acaaggcagc caccaaagta aagattatta ttcggggaaa acccaatgaa   1260
ggagtcgtta caaaaatgcc atttgtacca acaaaaatact ataagccttc ctgatttact   1320
tctgtattta tatcttaaac atttcctaat tgctctctcc cttgttgaca aattttccca   1380
taatcgagtg ttacagtcac tgttaatgac ttaaaaaaaa aaaaaaaaaa a            1431
```

<210> SEQ ID NO 68
<211> LENGTH: 407
<212> TYPE: PRT
<213> ORGANISM: Glycine max

<400> SEQUENCE: 68

```
Met Arg Gly Gly Leu Trp Gln Leu Gly Gln Ser Ile Thr Arg Arg Leu
 1               5                  10                  15

Ala His Gly Asp Lys Lys Ala Val Ala Arg Arg Cys Phe Ala Ser Glu
            20                  25                  30

Ala Glu Leu Lys Lys Thr Val Phe His Asp Phe His Val Ala His Gly
        35                  40                  45

Gly Lys Met Val Pro Phe Ala Gly Trp Ser Met Pro Ile Gln Tyr Lys
    50                  55                  60

Asp Ser Ile Met Asp Ser Thr Ile Asn Cys Arg Glu Asn Gly Ser Leu
65                  70                  75                  80

Phe Asp Val Ser His Met Cys Gly Leu Ser Leu Lys Gly Lys Asp Ala
                85                  90                  95

Ala Pro Phe Leu Glu Lys Leu Val Ile Ala Asp Val Ala Gly Leu Ala
            100                 105                 110

Pro Gly Thr Gly Thr Leu Thr Val Phe Thr Asn Glu Lys Gly Gly Ala
        115                 120                 125

Ile Asp Asp Ser Val Ile Thr Lys Val Thr Asp His Ile Tyr Leu
    130                 135                 140

Val Val Asn Ala Gly Cys Arg Asp Lys Asp Leu Ala His Ile Glu Glu
```

```
                145                 150                 155                 160
His Met Lys Ala Phe Lys Ala Lys Gly Gly Asp Val Ser Trp His Ile
                    165                 170                 175

His Asp Glu Arg Ser Leu Leu Ala Leu Gln Gly Pro Leu Ala Ala Pro
                180                 185                 190

Val Leu Gln His Leu Thr Lys Glu Asp Leu Ser Lys Leu Tyr Phe Gly
            195                 200                 205

Glu Phe Arg Val Leu Asp Ile Asn Gly Ser Glu Cys Phe Leu Thr Arg
        210                 215                 220

Thr Gly Tyr Thr Gly Glu Asp Gly Phe Glu Ile Ser Val Pro Ser Glu
225                 230                 235                 240

His Gly Val Asp Leu Ala Lys Ala Ile Leu Glu Lys Ser Glu Gly Lys
                245                 250                 255

Val Arg Leu Thr Gly Leu Gly Ala Arg Asp Ser Leu Arg Leu Glu Ala
                260                 265                 270

Gly Leu Cys Leu Tyr Gly Asn Asp Met Glu Gln His Ile Thr Pro Ile
            275                 280                 285

Glu Ala Gly Leu Thr Trp Ala Ile Gly Lys Arg Arg Ala Glu Gly
        290                 295                 300

Gly Phe Leu Gly Ala Asp Val Ile Leu Lys Gln Leu Glu Gly Pro
305                 310                 315                 320

Lys Ile Arg Arg Val Gly Phe Phe Ser Ser Gly Pro Pro Arg Ser
                325                 330                 335

His Ser Glu Ile Gln Asp Glu Gly Gly Asn Asn Ile Gly Glu Ile Thr
                340                 345                 350

Ser Gly Gly Phe Ser Pro Cys Leu Gln Lys Asn Ile Ala Met Gly Tyr
            355                 360                 365

Val Lys Ser Gly Leu His Lys Ala Ala Thr Lys Val Lys Ile Ile Ile
        370                 375                 380

Arg Gly Lys Pro Asn Glu Gly Val Val Thr Lys Met Pro Phe Val Pro
385                 390                 395                 400

Thr Lys Tyr Tyr Lys Pro Ser
                405

<210> SEQ ID NO 69
<211> LENGTH: 1468
<212> TYPE: DNA
<213> ORGANISM: Triticum aestivum

<400> SEQUENCE: 69
gcacgaggct agctcacccg ccggggctcg ccacgatgag aggcctcctc gcgtgcgcca      60
ccctcgcccg ccgcgccgcc gcctcctccg cgcccgcgcg cgtccgccac ctggcgggcg     120
ccgcggaggc ggcggaggcc gagctcaaga ggacggcgct ctacgacttc cacgtcgccc     180
acggcggcaa gatggtgccg ttcgccggct ggagcatgcc catccagtac agggactcca     240
tcatggactc caccgtcaac tgccgcgcca acggcagcct cttcgacgtc gcccacatgt     300
gcggcctcag cctcaatggc cgcggggcca tccccttcct cgagtccctc gtcgtcgccg     360
acgtcgccgc gctcagggac ggcaccggca ccctcaccgt cttccaccaa gagcagggcg     420
gcgccatcga cgactccgtc atcgccaagg tcaccgacca ccacatctac ctcgtcgtca     480
acgccggatg cagggacaag gacctcgccc acatcgaggc gcacatggag gccttcaaca     540
agaagggcgg ggacgtcaag tggcacatcc acgacgacca tcgctgctc gcattgcagg     600
gtcctcttgc tgcacctact ctgcagttgc tgacgaaaga agatttgagc aaaatgtact     660
```

```
tcagtgactt caagatgatt gacatcaatg gatatgcatg ctttctgacg agaactggct    720
acaccggcga agatggtttt gagatctctg ttccgtcaga gaatgcagtg gatcttgcag    780
aggccatcct agagagatcg gaaggcaagg tgcggctgac cggcttgggc gcccgtgaca    840
gtctccgact ggaggcaggc ctgtgcctgt acggcaacga catggagcag cacatcacgc    900
cggtggaagc cggcctctca tgggcgatcg gcaagaggag gagggcagag gcggttttcc    960
tgggcgcaga cgtgatcctg aagcagctcc aggaagggcc aaagatcagg cgcgtgggca   1020
tggtcacgca ggggccgccc gcgcggagcc acagcgagct ggtgagcggc tcggggggaga  1080
ggatcggcga ggtgaccagc ggagggttca gcccgtgcct gaagaagaac atcgctatgg   1140
gctacgtgaa gtcgggaatg cacaaggctg ggacggagtt gaaggtggtc gttcgcggga   1200
agtcctacga cgccgtggtc accaagatgc cgttcgtgcc caccaagtac tacaagccct   1260
cgtagattat attcttgtac agagggacgc cttgcgtttc tcttttgtcg ttgcggcttg   1320
ttcttggcag attggttaag cattgcaact gtaacttctg tgagattgtc ttacggttca   1380
catttcatgt atgcctgcct aataagcctt cttttcccaa atacaaagca tgcatgtgcc   1440
tatgtgaaga aaaaaaaaaa aaaaaaaa                                      1468
```

<210> SEQ ID NO 70
<211> LENGTH: 401
<212> TYPE: PRT
<213> ORGANISM: Triticum aestivum

<400> SEQUENCE: 70

```
Thr Leu Ala Arg Arg Ala Ala Ser Ser Ala Pro Ala Arg Val Arg
 1               5                  10                  15

His Leu Ala Gly Ala Ala Glu Ala Ala Glu Ala Glu Leu Lys Arg Thr
                20                  25                  30

Ala Leu Tyr Asp Phe His Val Ala His Gly Gly Lys Met Val Pro Phe
            35                  40                  45

Ala Gly Trp Ser Met Pro Ile Gln Tyr Arg Asp Ser Ile Met Asp Ser
        50                  55                  60

Thr Val Asn Cys Arg Ala Asn Gly Ser Leu Phe Asp Val Ala His Met
65                  70                  75                  80

Cys Gly Leu Ser Leu Asn Gly Arg Gly Ala Ile Pro Phe Leu Glu Ser
                85                  90                  95

Leu Val Val Ala Asp Val Ala Ala Leu Arg Asp Gly Thr Gly Thr Leu
            100                 105                 110

Thr Val Phe Thr Asn Glu Gln Gly Gly Ala Ile Asp Asp Ser Val Ile
        115                 120                 125

Ala Lys Val Thr Asp His His Ile Tyr Leu Val Val Asn Ala Gly Cys
    130                 135                 140

Arg Asp Lys Asp Leu Ala His Ile Glu Ala His Met Glu Ala Phe Asn
145                 150                 155                 160

Lys Lys Gly Gly Asp Val Lys Trp His Ile His Asp Arg Ser Leu
                165                 170                 175

Leu Ala Leu Gln Gly Pro Leu Ala Ala Pro Thr Leu Gln Leu Leu Thr
            180                 185                 190

Lys Glu Asp Leu Ser Lys Met Tyr Phe Ser Asp Phe Lys Met Ile Asp
        195                 200                 205

Ile Asn Gly Tyr Ala Cys Phe Leu Thr Arg Thr Gly Tyr Thr Gly Glu
    210                 215                 220
```

-continued

```
Asp Gly Phe Glu Ile Ser Val Pro Ser Glu Asn Ala Val Asp Leu Ala
225                 230                 235                 240

Glu Ala Ile Leu Glu Arg Ser Glu Gly Lys Val Arg Leu Thr Gly Leu
                245                 250                 255

Gly Ala Arg Asp Ser Leu Arg Leu Glu Ala Gly Leu Cys Leu Tyr Gly
                260                 265                 270

Asn Asp Met Glu Gln His Ile Thr Pro Val Glu Ala Gly Leu Ser Trp
            275                 280                 285

Ala Ile Gly Lys Arg Arg Arg Ala Glu Gly Gly Phe Leu Gly Ala Asp
            290                 295                 300

Val Ile Leu Lys Gln Leu Gln Glu Gly Pro Lys Ile Arg Arg Val Gly
305                 310                 315                 320

Met Val Thr Gln Gly Pro Pro Ala Arg Ser His Ser Glu Leu Val Ser
                325                 330                 335

Gly Ser Gly Glu Arg Ile Gly Glu Val Thr Ser Gly Gly Phe Ser Pro
                340                 345                 350

Cys Leu Lys Lys Asn Ile Ala Met Gly Tyr Val Lys Ser Gly Met His
                355                 360                 365

Lys Ala Gly Thr Glu Leu Lys Val Val Arg Gly Lys Ser Tyr Asp
            370                 375                 380

Ala Val Val Thr Lys Met Pro Phe Val Pro Thr Lys Tyr Tyr Lys Pro
385                 390                 395                 400

Ser
```